United States Patent
Liang et al.

(10) Patent No.: US 11,872,202 B2
(45) Date of Patent: *Jan. 16, 2024

(54) PLEUROMUTILIN CINNAMIC ACID ESTER COMPOUNDS WITH ACTIVITIES AGAINST ANTIBIOTIC-RESISTANT INFECTIONS

(71) Applicants: Chengyuan Liang, Xi'an (CN); Xiuding Yang, Xi'an (CN); Liang Xin, Xi'an (CN); Juan Xia, Xi'an (CN); Yuqing Zhao, Xi'an (CN); Jie Zhang, Xi'an (CN); Lei Tian, Xi'an (CN); Jingyi Li, Xi'an (CN); Shaojun Zhang, Xi'an (CN); Qianqian Zhao, Xi'an (CN)

(72) Inventors: Chengyuan Liang, Xi'an (CN); Xiuding Yang, Xi'an (CN); Liang Xin, Xi'an (CN); Juan Xia, Xi'an (CN); Yuqing Zhao, Xi'an (CN); Jie Zhang, Xi'an (CN); Lei Tian, Xi'an (CN); Jingyi Li, Xi'an (CN); Shaojun Zhang, Xi'an (CN); Qianqian Zhao, Xi'an (CN)

(73) Assignee: SHAANXI UNIVERSITY OF SCIENCE AND TECHNOLOGY, Shaanxi (CN)

( * ) Notice: Subject to any disclaimer, the term of this patent is extended or adjusted under 35 U.S.C. 154(b) by 129 days.

This patent is subject to a terminal disclaimer.

(21) Appl. No.: 17/695,741

(22) Filed: Mar. 15, 2022

(65) Prior Publication Data
US 2023/0172889 A1 Jun. 8, 2023

(30) Foreign Application Priority Data
Dec. 6, 2021 (CN) .......................... 202111479806.X

(51) Int. Cl.
*A61K 31/216* (2006.01)
*A61P 31/04* (2006.01)

(52) U.S. Cl.
CPC ............ *A61K 31/216* (2013.01); *A61P 31/04* (2018.01)

(58) Field of Classification Search
CPC .................................................... A61K 31/216
See application file for complete search history.

(56) References Cited

U.S. PATENT DOCUMENTS 11,510,905 B1 * 11/2022 Liang ...................... A61P 31/04

* cited by examiner

*Primary Examiner* — Svetlana M Ivanova
(74) *Attorney, Agent, or Firm* — SZDC Law PC

(57) ABSTRACT

A pleuromutilin cinnamic acid ester compound with activities against antibiotic-resistant infections having the following formula (I)

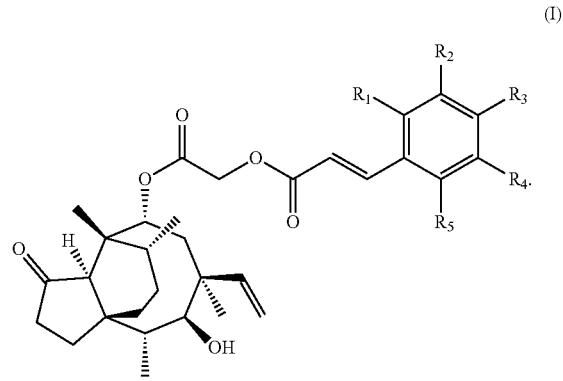

$R_1$, $R_2$, $R_3$, $R_4$ and $R_5$ are independently hydrogen, halogen, nitro, cyano, methoxy, trifluoromethyl, benzyloxy, aryl or dimethylamino.

2 Claims, No Drawings

PLEUROMUTILIN CINNAMIC ACID ESTER COMPOUNDS WITH ACTIVITIES AGAINST ANTIBIOTIC-RESISTANT INFECTIONS

The present application claims priority to Chinese Patent Application No. 202111479806.X, filed on Dec. 6, 2021, which is incorporated by reference for all purposes as if fully set forth herein.

TECHNICAL FIELD

The present invention relates to the field of medicinal chemistry, and specifically, a pleuromutilin cinnamic acid ester compound with activities against antibiotic-resistant infections and methods of preparing the same.

BACKGROUND TECHNIQUE

Because of the overuse of antibiotics, a variety of drug-resistant "superbugs" have begun to spread around the world, posing new threats to human health. The emergence of drug-resistant bacteria increases the difficulty of treating infectious diseases. With the increase of drug-resistant bacteria, the scope and degree of drug resistance are also increasing. The drug resistance problem of Gram-positive bacteria is more serious. Methicillin-resistant *Staphylococcus aureus* (MRSA) is a common and highly virulent bacterium in clinical practice. There is an urgent for new drugs that can deal with multidrug-resistant bacteria.

Pleuromutilin is a diterpenoid with a rigid 5-6-8 tricyclic carbon skeleton isolated from two natural basidiomycetes (*Pleurotus mutilus* and *Pleurotus passeckerianus*).

Cinnamic acid, also known as cinnamic acid and cinnamic acid, is a fine chemical synthesis intermediate. Because of its good antiseptic and bactericidal effect, it is widely used in fruit and vegetable preservation, food additives and pharmaceutical industry.

There is no report on the synthesis of a pleuromutilin cinnamic acid ester compound.

SUMMARY OF THE INVENTION

In one embodiment, the present application discloses a pleuromutilin cinnamic acid ester compound with activities against antibiotic-resistant infections having the following formula (I):

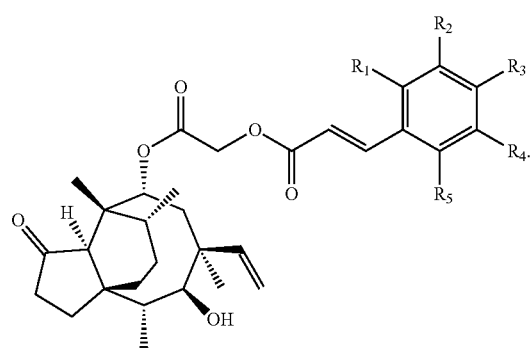

(I)

$R_1$, $R_2$, $R_3$, $R_4$ and $R_5$ are independently hydrogen, halogen, nitro, cyano, methoxy, trifluoromethyl, benzyloxy, aryl or dimethylamino.

In another embodiment, the compound is selected from the group consisting of

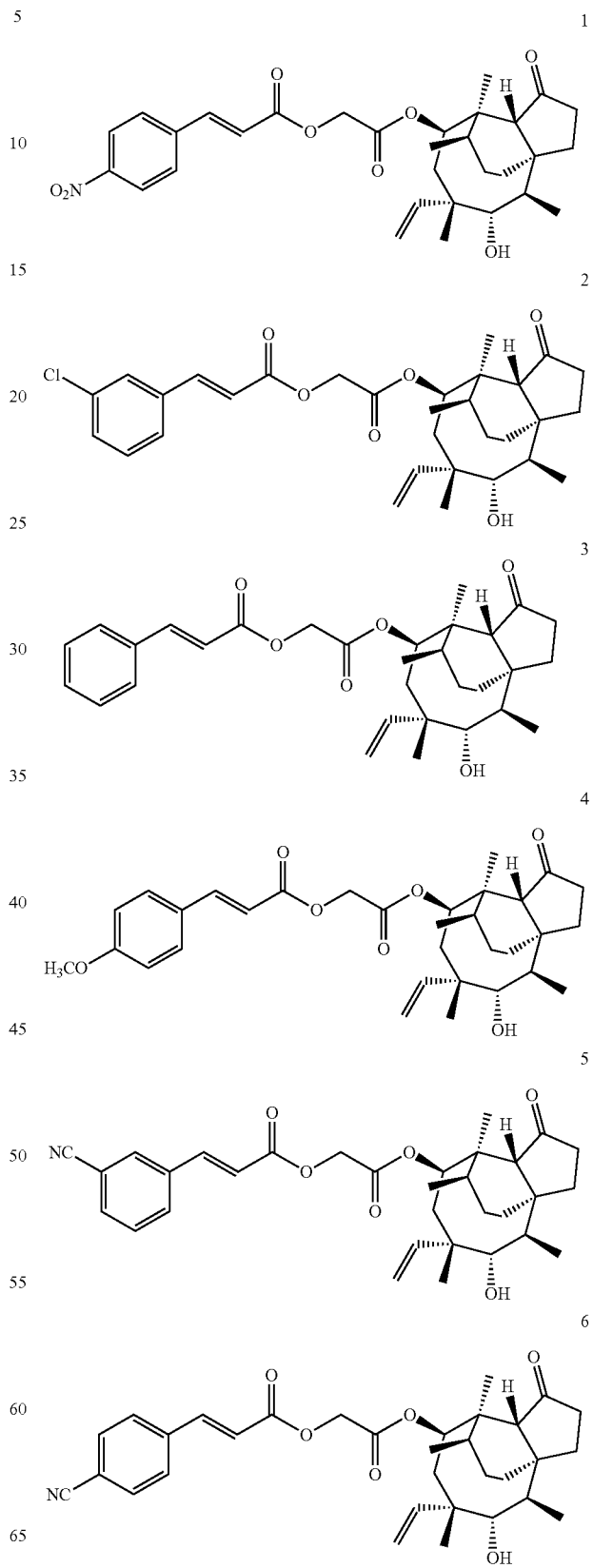

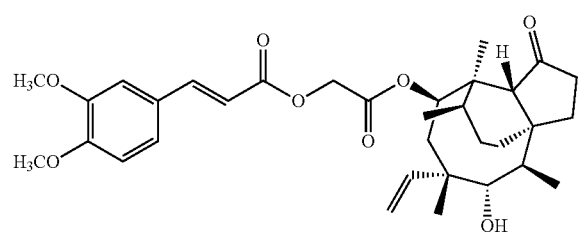
7
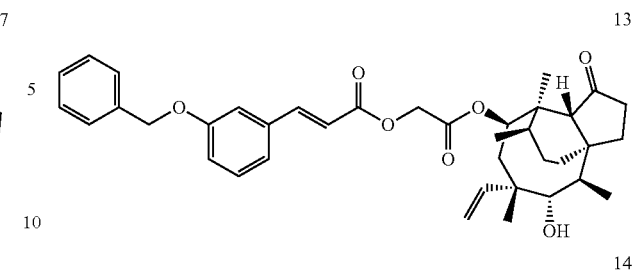
13
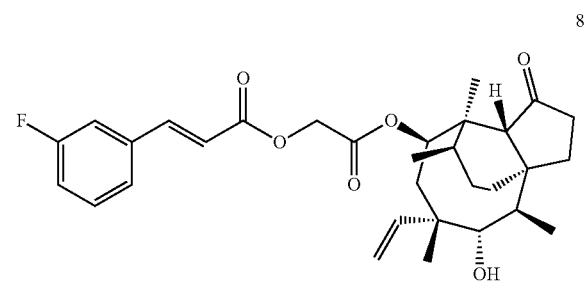
8
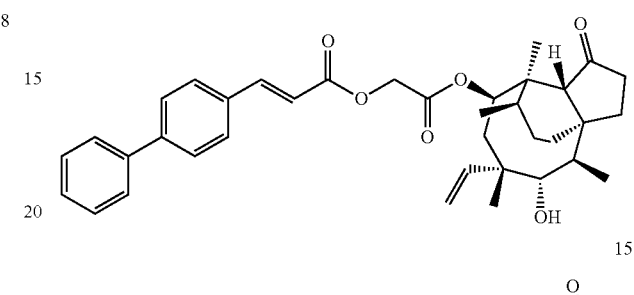
14
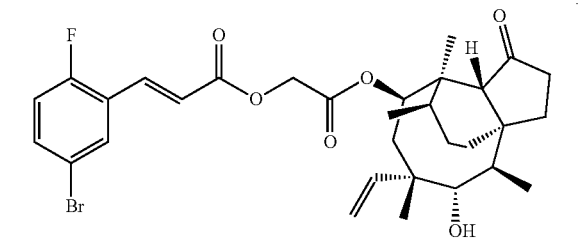
9
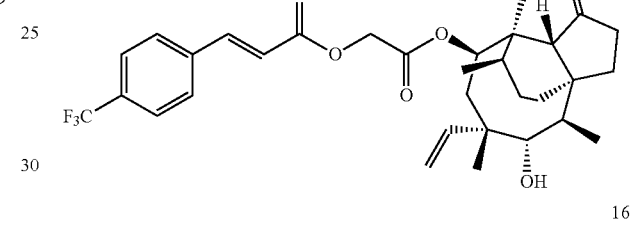
15
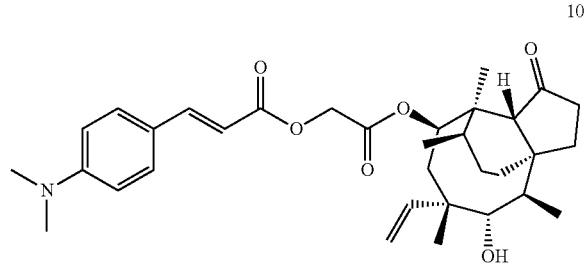
10
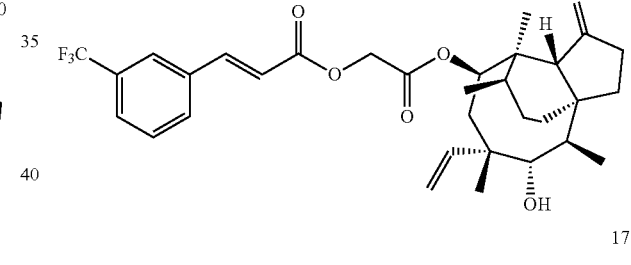
16
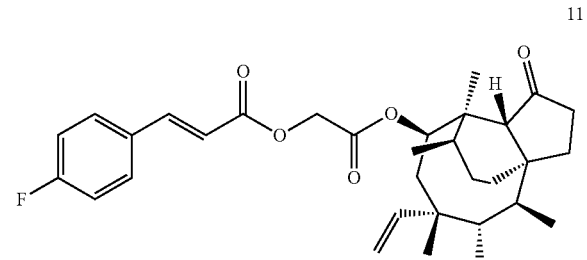
11
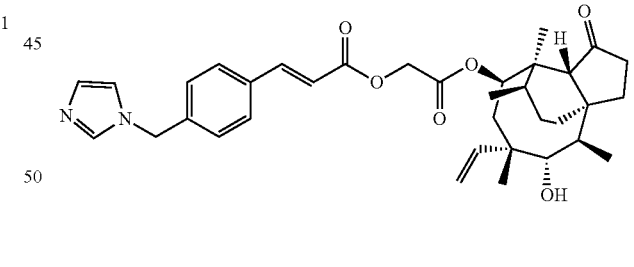
17
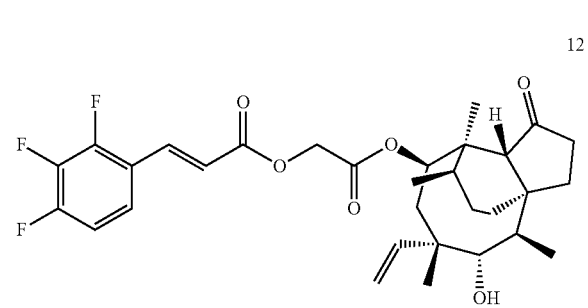
12
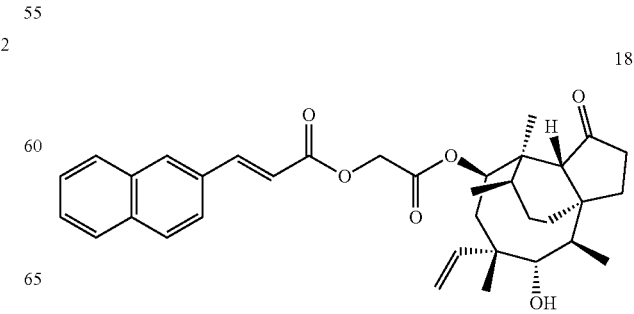
18

Synthesis Route 1:

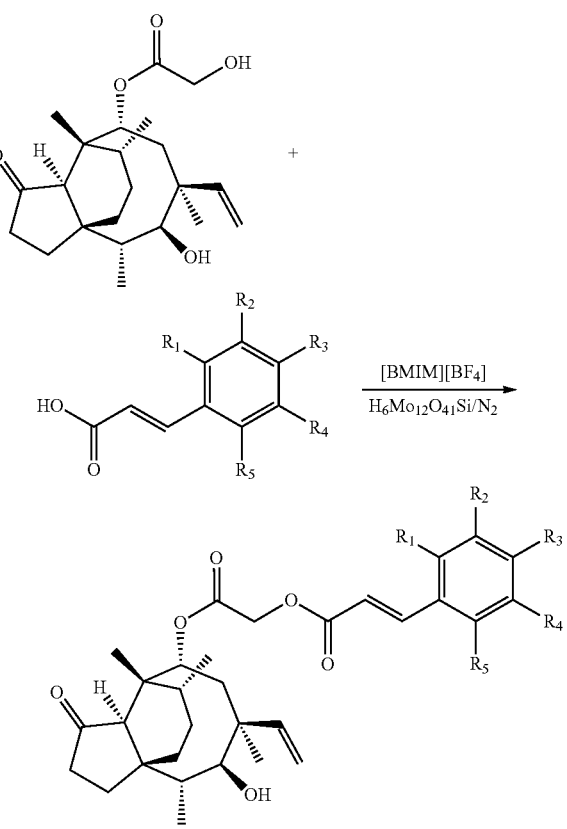

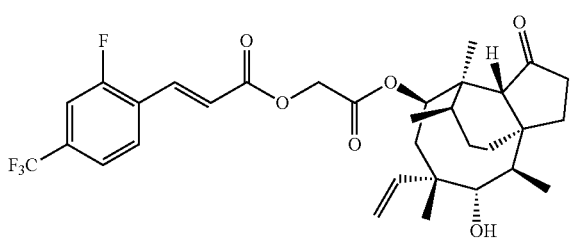

19

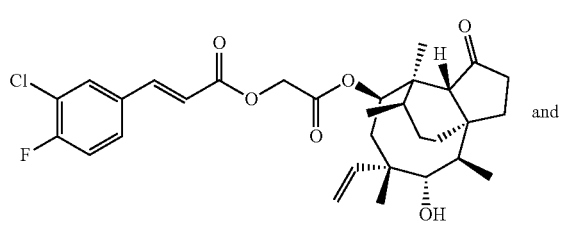

20 and 20

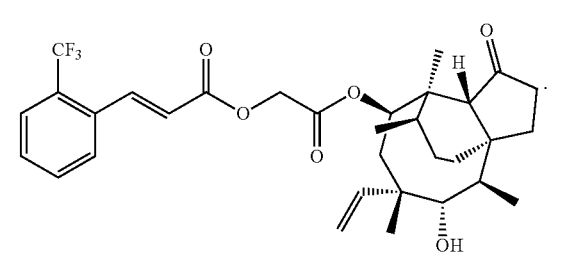

21

[BMIM] [BF$_4$]: 1-butyl-3-methylimidazolium tetrafluoroborate
H$_6$Mo$_{12}$O$_{41}$Si: 12-molybdosilicic acid hydrate Synthesis Route 2:

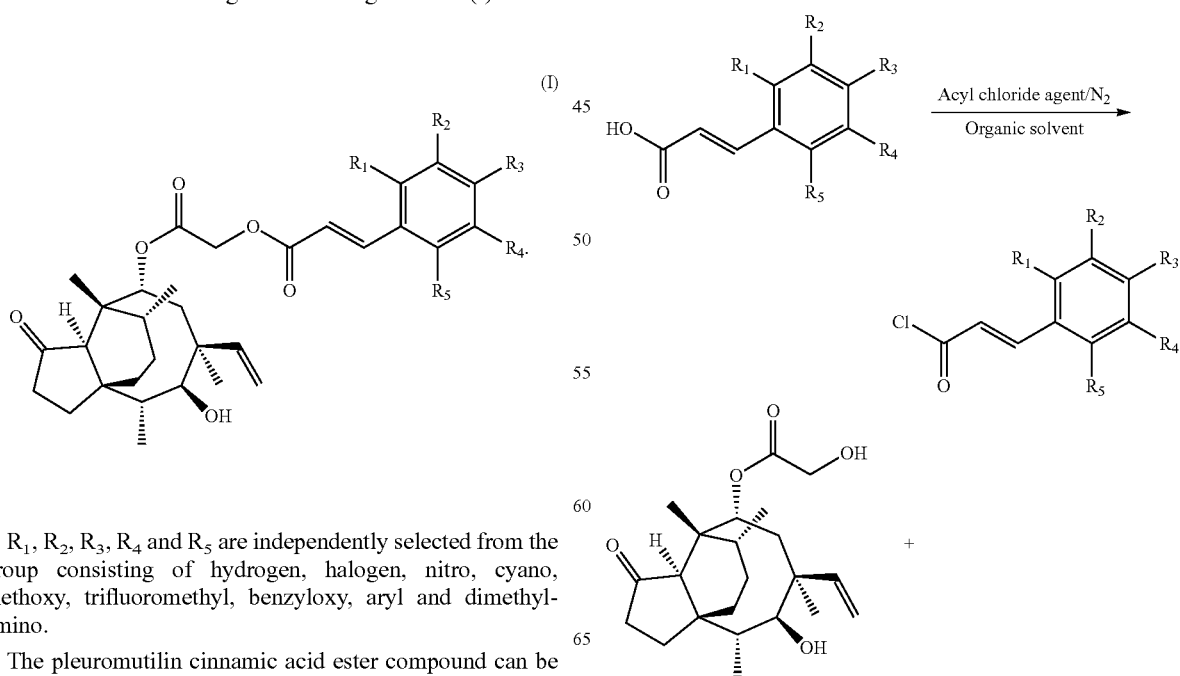

DETAILED DESCRIPTION

The present application discloses a pleuromutilin cinnamic acid ester compound with activities against antibiotic-resistant infections having the following formula (I):

(I)

$R_1$, $R_2$, $R_3$, $R_4$ and $R_5$ are independently selected from the group consisting of hydrogen, halogen, nitro, cyano, methoxy, trifluoromethyl, benzyloxy, aryl and dimethylamino.

The pleuromutilin cinnamic acid ester compound can be prepared by the following methods.

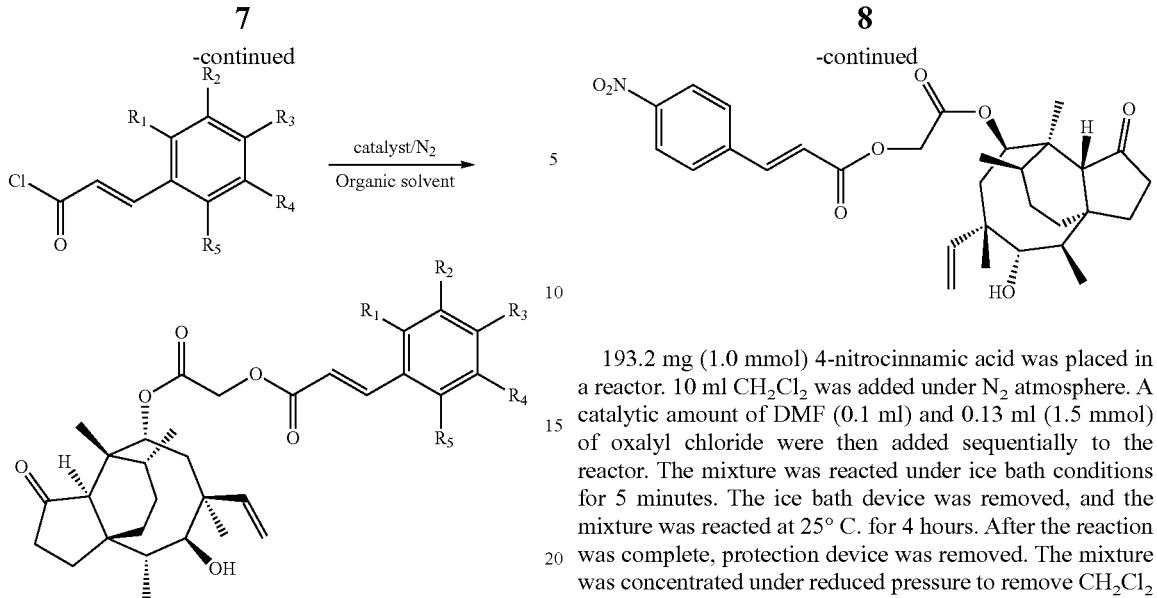

Acyl chloride reagent (acid chloride reagent): oxalyl chloride, thionyl chloride or phosphorus pentachloride, preferably, oxalyl chloride.

Catalyst: triethylamine, pyridine or DMAP, preferably, triethylamine.

1. Preparation of Compounds 1-21

Example 1

Preparation of (E)-2-(((3aR,4R,5R,8S,9R,12R)-8-hydroxy-4,7,9,12-tetramethyl-3-oxo-7-vinyl decahydro-4,9a-propanocyclopenta[8]annulen-5-yl)oxy)-2-oxoethyl 3-(4-nitrophenyl)acrylate (E)-2-((3aR, 4R, 5R, 7S, 8S, 9R, 9aS, 12R)

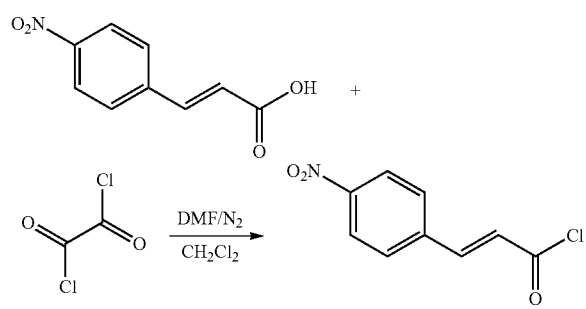

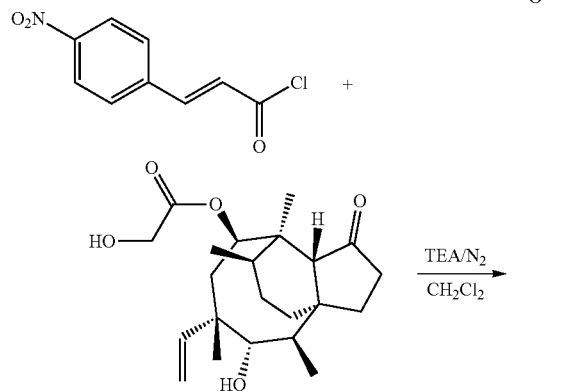

193.2 mg (1.0 mmol) 4-nitrocinnamic acid was placed in a reactor. 10 ml CH$_2$Cl$_2$ was added under N$_2$ atmosphere. A catalytic amount of DMF (0.1 ml) and 0.13 ml (1.5 mmol) of oxalyl chloride were then added sequentially to the reactor. The mixture was reacted under ice bath conditions for 5 minutes. The ice bath device was removed, and the mixture was reacted at 25° C. for 4 hours. After the reaction was complete, protection device was removed. The mixture was concentrated under reduced pressure to remove CH$_2$Cl$_2$ and excess oxalyl chloride to obtain 4-nitrocinnamoyl chloride for next step. 454.2 mg (1.2 mmol) of pleuromutilin was placed in a reactor, and 10 ml of CH$_2$Cl$_2$ and 0.14 ml (1.0 mmol) of triethylamine were added successively under N$_2$ atmosphere. 4-Nitrocinnamoyl chloride was dissolved in 5 ml CH$_2$C1$_2$ was added dropwise to the reactor with a constant pressure burette. The mixture was reacted under ice bath conditions for 5 minutes. The ice bath device was removed, and the mixture was reacted at room temperature for 5 hours. After the reaction was complete, the reaction mixture was concentrated under reduced pressure to remove CH$_2$Cl$_2$. The obtained concentrated solution was washed with water, extracted with ethyl acetate, separated and purified by column chromatography, and dried to obtain 512.2 mg of the target compound with a yield of 92.5%.

$^1$H NMR (400 MHz, CDCl$_3$) δ 8.30 (d, J=8.2 Hz, 2H), 7.83 (d, J=16.0 Hz, 1H), 7.73 (d, J=8.4 Hz, 2H), 6.67 (d, J=16.1 Hz, 1H), 6.52 (dd, J=17.3, 11.0 Hz, 1H), 5.86 (d, J=8.5 Hz, 1H), 5.39 (d, J=10.9 Hz, 1H), 5.26 (d, J=17.3 Hz, 1H), 4.71 (dd, J=16.0 Hz, 2H), 3.41 (d, J=6.4 Hz, 1H), 2.36 (t, J=7.0 Hz, 1H), 2.27 (q, J=10.1, 9.3 Hz, 2H), 2.17-2.07 (m, 2H), 1.88-1.51 (m, 7H), 1.49 (s, 3H), 1.41 (d, J=15.8 Hz, 2H), 1.23 (s, 3H), 0.92 (d, J=6.8 Hz, 3H), 0.84 (d, J=6.8 Hz, 3H).

$^{13}$C NMR (101 MHz, CDCl$_3$) δ 216.91, 166.53, 165.11, 148.71, 143.19, 140.18, 138.80, 130.46, 128.83, 124.24, 123.22, 121.07, 117.38, 74.58, 69.92, 61.62, 58.09, 45.46, 44.63, 44.06, 41.89, 36.68, 36.07, 34.45, 30.40, 26.84, 26.45, 24.84, 16.64, 14.79, 11.47.

Example 2

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(3-chlorophenyl)acrylate

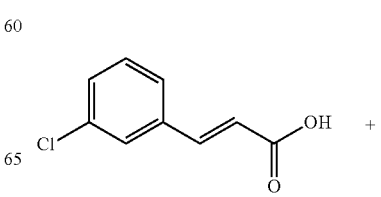

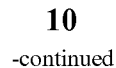

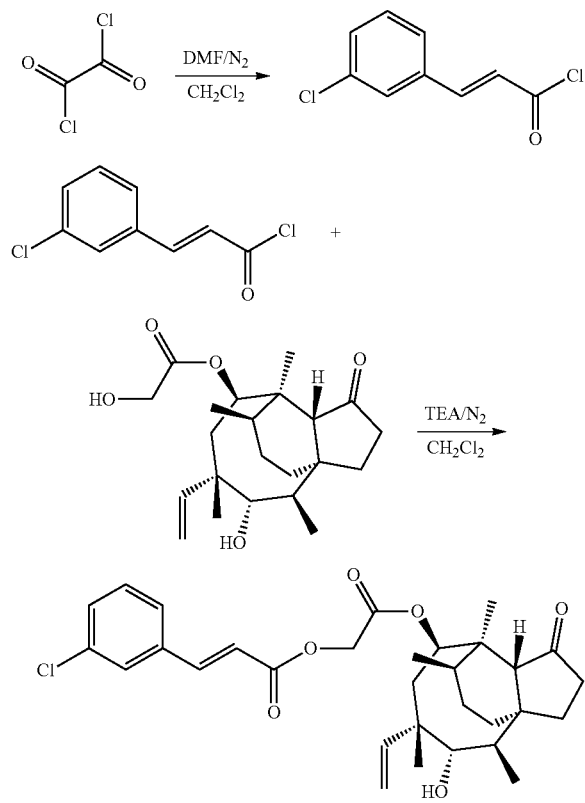
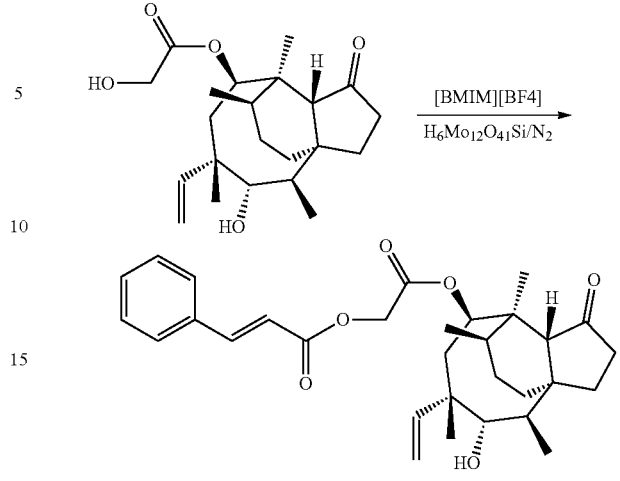

The target compound was prepared in a similar way as Example 1. The yield is 494.2 mg, 91.0%

$^1$H NMR (400 MHz, CDCl$_3$) δ (ppm): 7.75 (d, J=16.0 Hz, 1H), 7.57 (s, 1H), 7.42 (m, 3H), 6.58 (s, 1H), 6.54-6.50 (m, 1H), 5.87 (d, J=8.5 Hz, 1H), 5.44-5.25 (m, 2H), 4.73 (dd, J=38.8, 16.0 Hz, 2H), 3.42 (d, J=6.4 Hz, 1H), 2.39 (t, J=7.2 Hz, 1H), 2.32-2.20 (m, 2H), 2.18-2.12 (m, 2H), 1.85-1.52 (m, 7H), 1.51 (s, 3H), 1.45-1.41 (m, 2H), 1.24 (s, 3H), 0.94 (d, J=7.0 Hz, 3H), 0.85 (d, J=7.0 Hz, 3H).

$^{13}$C-NMR (101 MHz, CDCl$_3$) δ (ppm): 216.77, 166.64, 165.54, 144.52, 138.81, 135.98, 135.00, 130.42, 130.16, 127.94, 126.33, 118.29, 117.32, 74.59, 69.78, 61.44, 58.10, 45.44, 44.64, 44.05, 41.89, 36.69, 36.05, 34.42, 30.42, 26.83, 26.42, 24.83, 16.60, 14.78, 11.40.

148.2 mg (1 mmol) of cinnamic acid, 454.2 mg (1.2 mmol) of pleuromutilin and 17.1 mg (0.01 mmol) of silicomolybdic acid were added in a 250 mL reactor. 142.9 mL of ionic liquid 1-butyl-3-methylimidazolium tetrafluoroborate was added to fully dissolve all the chemicals in the reactor. The reaction mixture was reacted under N$_2$ at 20° C. for 4.5 hours. The reaction was monitored to completion by thin layer chromatography. The reaction mixture was separated into layers in the separatory funnel. The ionic liquid layer and the ester layer were separated, and the obtained ester layer includes a crude cinnamate derivative. After recrystallization and drying with 50 mL of methanol, 475.4 mg of the target compound were obtained, a total yield of 93.5%.

$^1$H NMR (400 MHz, CDCl$_3$) δ 7.81 (d, J=16.0 Hz, 1H), 7.59-7.56 (m, 2H), 7.47-7.40 (m, 3H), 6.62-6.47 (m, 2H), 5.85 (d, J=8.4 Hz, 1H), 5.40 (d, J=11.0 Hz, 1H), 5.26 (d, J=17.4 Hz, 1H), 4.79-4.58 (m, 2H), 3.40 (s, 1H), 2.37 (t, J=7.3 Hz, 1H), 2.32-2.19 (m, 2H), 2.16-2.06 (m, 2H), 1.84-1.51 (m, 6H), 1.49 (s, 3H), 1.47-1.35 (m, 2H), 1.22 (s, 3H), 1.18-1.10 (m, 1H), 0.92 (d, J=6.9 Hz, 4H), 0.84 (d, J=6.8 Hz, 3H).

$^{13}$C NMR (101 MHz, CDCl$_3$) δ 216.98, 166.84, 166.02, 146.28, 138.77, 134.14, 130.62, 128.95, 128.24, 117.41, 116.72, 74.57, 69.67, 61.36, 58.10, 45.45, 44.58, 44.03, 41.88, 36.71, 36.02, 34.46, 30.42, 26.83, 26.38, 24.83, 16.67, 14.80, 11.48.

Example 3

Preparation of 2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl cinnamate

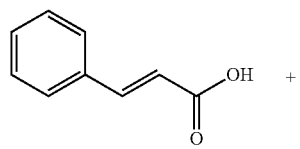

Example 4

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(4-methoxyphenyl)acrylate

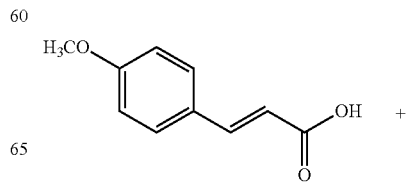

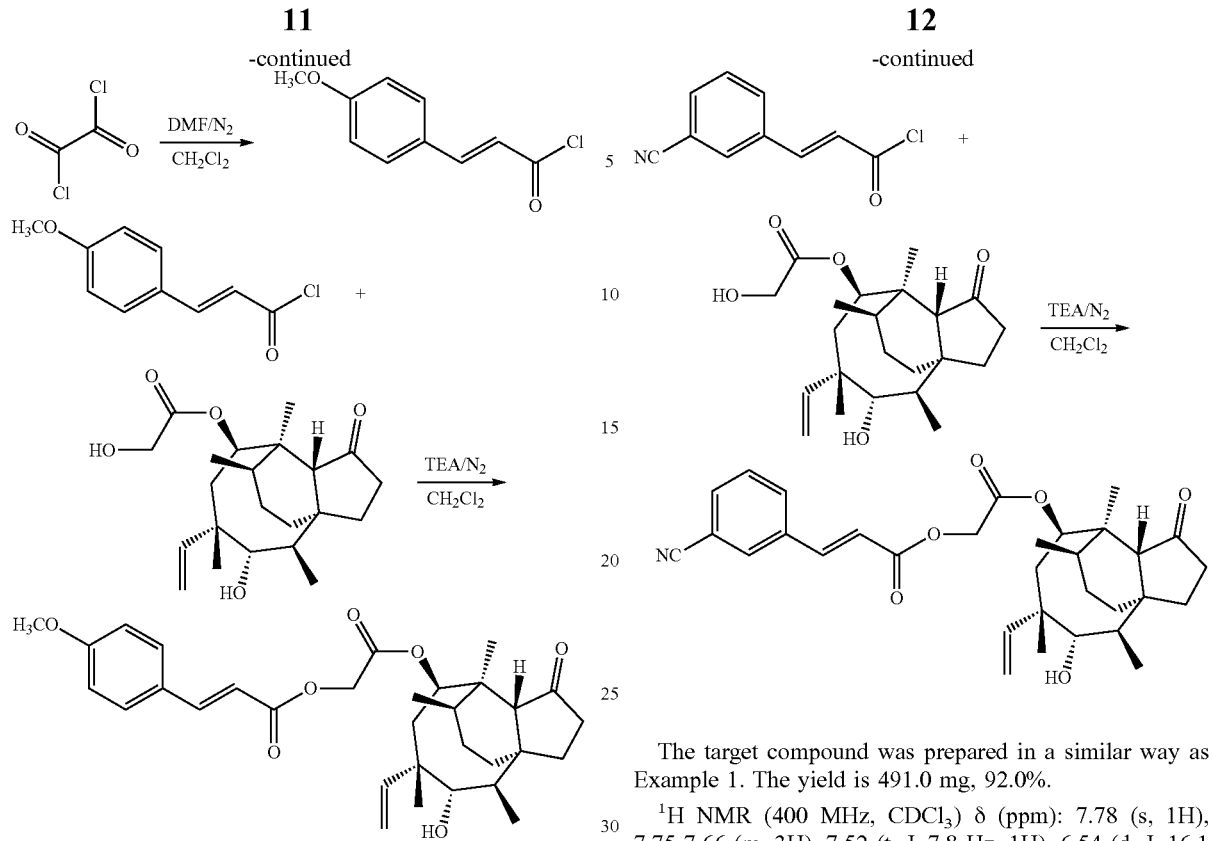

The target compound was prepared in a similar way as Example 1. The yield is 492.7 mg, 88.5%.

¹H NMR (400 MHz, CDCl₃) δ 7.76 (d, J=15.8 Hz, 1H), 7.52 (d, J=8.3 Hz, 2H), 6.95 (d, J=8.3 Hz, 2H), 6.53 (dd, J=17.4, 11.1 Hz, 1H), 6.41 (d, J=15.9 Hz, 1H), 5.85 (d, J=8.4 Hz, 1H), 5.39 (d, J=11.0 Hz, 1H), 5.25 (d, J=17.4 Hz, 1H), 4.75-4.60 (m, 2H), 3.88 (s, 3H), 3.40 (d, J=6.4 Hz, 1H), 2.37 (t, J=7.1 Hz, 1H), 2.29-2.18 (m, 2H), 2.14-2.09 (m, 2H), 1.83-1.54 (m, 6H), 1.49-1.39 (m, 6H), 1.22 (s, 3H), 0.91 (d, J=6.9 Hz, 3H), 0.84 (d, J=7.0 Hz, 3H).

¹³C NMR (101 MHz, CDCl₃) δ 216.98, 166.99, 166.34, 161.67, 145.94, 138.82, 129.96, 126.94, 117.39, 114.40, 114.16, 74.60, 69.62, 61.27, 58.13, 55.41, 45.47, 44.61, 44.05, 41.90, 36.74, 36.04, 34.47, 30.44, 26.85, 26.39, 24.85, 16.67, 14.82, 11.48.

Example 5

Preparation of (E)-2-(((3aR,4R,5R,8S,9R,12R)-8-hydroxy-4,7,9,12-tetramethyl-3-oxo-7-vinyldeca-hydro-4,9a-propanocyclopenta[8]annulen-5-yl)oxy)-2-oxoethyl 3-(3-cyanophenyl)acrylate The target compound was prepared in a similar way as Example 1. The yield is 491.0 mg, 92.0%.

¹H NMR (400 MHz, CDCl₃) δ (ppm): 7.78 (s, 1H), 7.75-7.66 (m, 3H), 7.52 (t, J=7.8 Hz, 1H), 6.54 (d, J=16.1 Hz, 1H), 6.46 (dd, J=17.4, 11.0 Hz, 1H), 5.81 (d, J=8.5 Hz, 1H), 5.34 (d, J=11.0 Hz, 1H), 5.21 (d, J=17.4 Hz, 1H), 4.67 (dd, J=36.4, 16.0 Hz, 2H), 3.36 (d, J=6.2 Hz, 1H), 2.32 (t, J=6.8 Hz, 1H), 2.25-2.16 (m, 2H), 2.11-2.05 (m, 2H), 1.79-1.60 (m, 4H), 1.56-1.47 (m, 3H), 1.44 (s, 3H), 1.41-1.34 (m, 2H), 1.18 (s, 3H), 0.87 (d, J=7.0 Hz, 3H), 0.78 (d, J=7.0 Hz, 3H).

¹³C-NMR (101 MHz, CDCl₃) δ (ppm): 216.74, 166.51, 165.19, 143.32, 138.81, 135.45, 133.44, 131.92, 131.46, 129.86, 119.59, 117.99, 117.32, 113.53, 74.60, 69.89, 61.55, 58.09, 45.44, 44.67, 44.06, 41.90, 36.68, 36.06, 34.42, 30.41, 26.83, 26.43, 24.83, 16.59, 14.77, 11.39.

Example 6

Preparation of (E)-2-(((3aR,4R,5R,8S,9R,12R)-8-hydroxy-4,7,9,12-tetramethyl-3-oxo-7-vinyldeca-hydro-4,9a-propanocyclopenta[8]annulen-5-yl)oxy)-2-oxoethyl 3-(4-cyanophenyl)acrylate

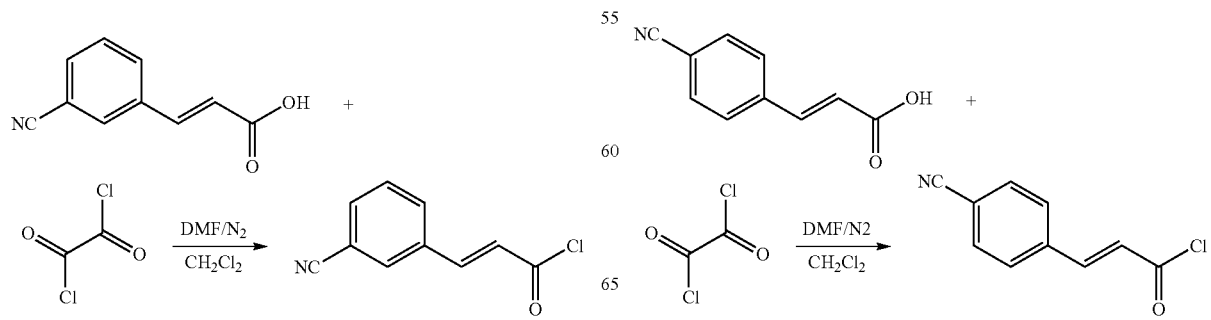

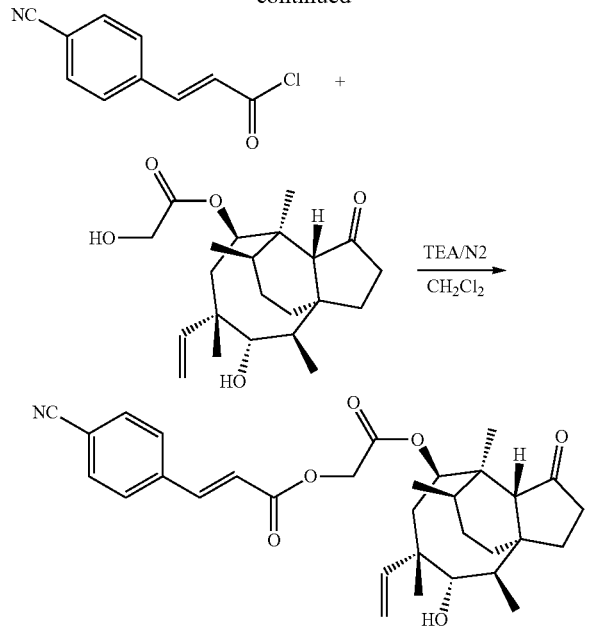

The target compound was prepared in a similar way as Example 1. The yield is 437.6 mg, 82%.

$^1$H NMR (400 MHz, CDCl3) δ 7.78 (d, J=16.1 Hz, 1H), 7.73 (d, J=8.3 Hz, 2H), 7.66 (d, J=8.4 Hz, 2H), 6.62 (d, J=16.0 Hz, 1H), 6.51 (dd, J=17.4, 11.0 Hz, 1H), 5.86 (d, J=8.5 Hz, 1H), 5.39 (d, J=11.0, 1H), 5.26 (d, J=17.4, 1H), 4.72 (dd, J=37.2, 16.0 Hz, 2H), 3.41 (d, J=6.5 Hz, 1H), 2.37 (t, J=6.8 Hz, 1H), 2.32-2.19 (m, 2H), 2.18-2.09 (m, 2H), 1.84-1.52 (m, 7H), 1.49 (s, 3H), 1.46-1.39 (m, 2H), 1.23 (s, 3H), 0.92 (d, J=6.9 Hz, 3H), 0.83 (d, J=7.0 Hz, 3H).

$^{13}$C NMR (101 MHz, CDCl3) δ 216.77, 166.52, 165.17, 143.68, 138.83, 138.41, 132.70, 128.53, 120.42, 118.22, 117.34, 113.79, 74.61, 69.93, 61.59, 58.10, 45.46, 44.68, 44.08, 41.91, 36.69, 36.08, 34.43, 30.42, 26.85, 26.45, 24.84, 16.61, 14.78, 11.41.

Example 7

Preparation of (E)-2-(((3aR,4R,5R,8S,9R,12R)-8-hydroxy-4,7,9,12-tetramethyl-3-oxo-7-vinyldeca-hydro-4,9a-propanocyclopenta[8]annulen-5-yl)oxy)-2-oxoethyl 3-(3,4-dimethoxyphenyl)acrylate

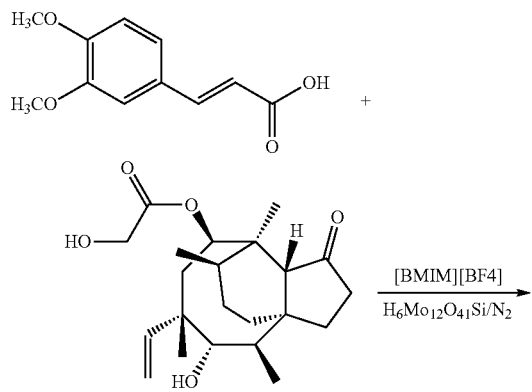

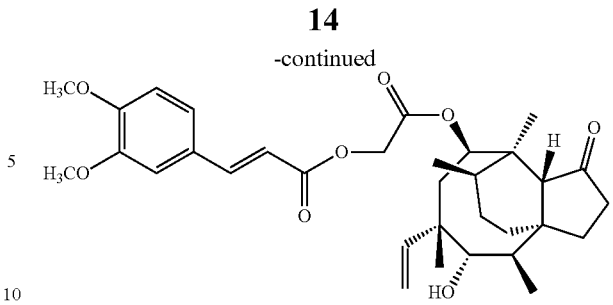

The target compound was prepared in a similar way as Example 3. The yield is 527.8 mg, 92.8%.

$^1$H NMR (400 MHz, CDCl$_3$) δ (ppm): 7.75 (d, J=15.9 Hz, 1H), 7.18-7.07 (m, 2H), 6.91 (d, J=8.3 Hz, 1H), 6.53 (dd, J=17.3, 11.0 Hz, 1H), 6.42 (d, J=15.9 Hz, 1H), 5.85 (d, J=8.5 Hz, 1H), 5.39 (d, J=10.9 Hz, 1H), 5.23 (t, J=17.0 Hz, 1H), 4.68 (dd, J=36.7, 16.0 Hz, 2H), 3.99-3.91 (m, 6H), 3.40 (s, 1H), 2.37 (t, J=6.8 Hz, 1H), 2.29-2.18 (m, 2H), 2.14-2.09 (m, 2H), 1.83-1.54 (m, 7H), 1.49 (s, 3H), 1.41 (m, 2H), 1.22 (s, 3H), 0.92 (d, J=6.8 Hz, 3H), 0.84 (d, J=6.9 Hz, 3H).

$^{13}$C-NMR (101 MHz, CDCl$_3$) δ (ppm): 216.79, 166.90, 166.17, 151.47, 149.31, 146.12, 138.85, 127.21, 122.89, 117.29, 114.42, 111.14, 109.86, 74.60, 69.67, 61.27, 58.12, 55.98, 55.91, 45.45, 44.65, 44.06, 41.90, 36.72, 36.06, 34.43, 30.43, 26.84, 26.43, 24.83, 16.61, 14.80, 11.40.

Example 8

Preparation of (E)-2-(((3aR,4R,5R,8S,9R,12R)-8-hydroxy-4,7,9,12-tetramethyl-3-oxo-7-vinyldeca-hydro-4,9a-propanocyclopenta[8]annulen-5-yl)oxy)-2-oxoethyl 3-(3-fluorophenyl)acrylate

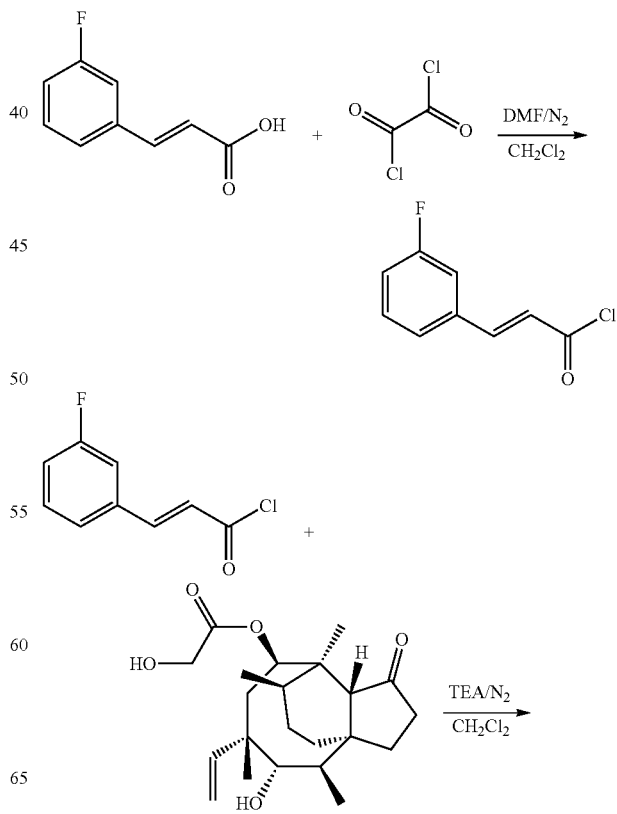

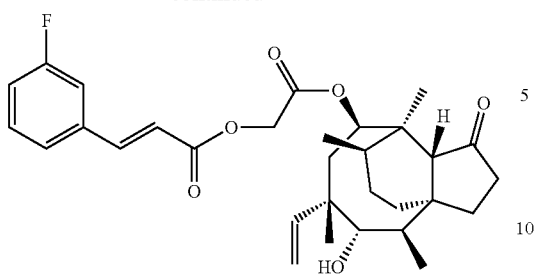

The target compound was prepared in a similar way as Example 1. The yield is 475.6 mg, 90.3%.

¹H NMR (400 MHz, CDCl₃) δ 7.76 (d, J=16.0 Hz, 1H), 7.45-7.31 (m, 2H), 7.26 (d, J=9.8 Hz, 1H), 7.14 (t, J=8.4 Hz, 1H), 6.59-6.46 (m, 2H), 5.85 (d, J=8.4 Hz, 1H), 5.40 (d, J=11.0 Hz, 1H), 5.26 (d, J=17.4 Hz, 1H), 4.69 (d, J=16.0 Hz, 2H), 3.40 (d, J=6.4 Hz, 1H), 2.37 (t, J=7.2 Hz, 1H), 2.32-2.18 (m, 2H), 2.18-2.04 (m, 2H), 1.88-1.51 (m, 6H), 1.49 (s, 3H), 1.46-1.31 (m, 2H), 1.22 (s, 3H), 1.19-1.09 (m, 1H), 0.92 (d, J=6.9 Hz, 3H), 0.83 (d, J=7.0 Hz, 3H).

¹³C NMR (101 MHz, CDCl₃) δ 216.94, 166.72, 165.66, 144.83, 138.79, 136.43, 130.58, 130.50, 124.24, 118.20, 117.60, 114.58, 114.36, 74.59, 69.77, 61.45, 58.11, 45.46, 44.62, 44.06, 41.90, 36.71, 36.05, 34.46, 30.43, 26.85, 26.40, 24.84, 16.66, 14.80, 11.47.

Example 9

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(5-bromo-2-fluorophenyl)acrylate

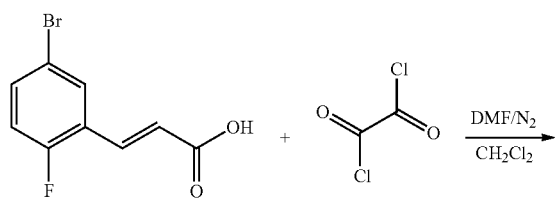

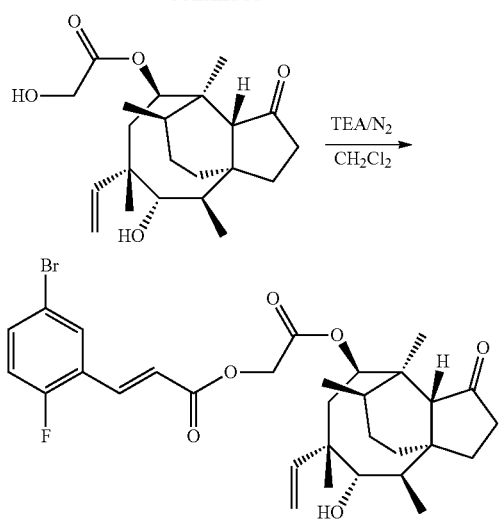

The target compound was prepared in a similar way as Example 1. The yield is 560.8 mg, 92.6%.

¹H NMR (400 MHz, CDCl₃) δ 7.78 (d, J=6.7 Hz, 1H), 7.70 (d, J=16.0 Hz, 1H), 7.53-7.45 (m, 1H), 7.19 (t, J=8.4 Hz, 1H), 6.58-6.44 (m, 2H), 5.86 (d, J=8.6 Hz, 1H), 5.40 (d, J=11.0 Hz, 1H), 5.26 (d, J=17.4 Hz, 1H), 4.69 (dd, J=40.0, 16.0 Hz, 2H), 3.41 (d, J=6.4 Hz, 1H), 2.37 (t, J=8.0 Hz, 1H), 2.32-2.21 (m, 2H), 2.18-2.08 (m, 2H), 1.86-1.50 (m, 6H), 1.49 (s, 3H), 1.41 (d, J=15.9 Hz, 2H), 1.23 (s, 3H), 1.21-1.13 (m, 1H), 0.92 (d, J=6.8 Hz, 3H), 0.83 (d, J=6.9 Hz, 3H).

¹³C NMR (101 MHz, CDCl₃) δ 216.78, 166.62, 165.43, 143.37, 138.80, 133.17, 128.87, 128.79, 117.95, 117.33, 117.14, 116.92, 74.59, 69.80, 61.45, 58.10, 45.44, 44.64, 44.05, 41.89, 36.69, 36.05, 34.43, 30.41, 26.83, 26.42, 24.83, 16.61, 14.78, 11.41.

Example 10

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(4-(dimethylamino)phenyl)acrylate

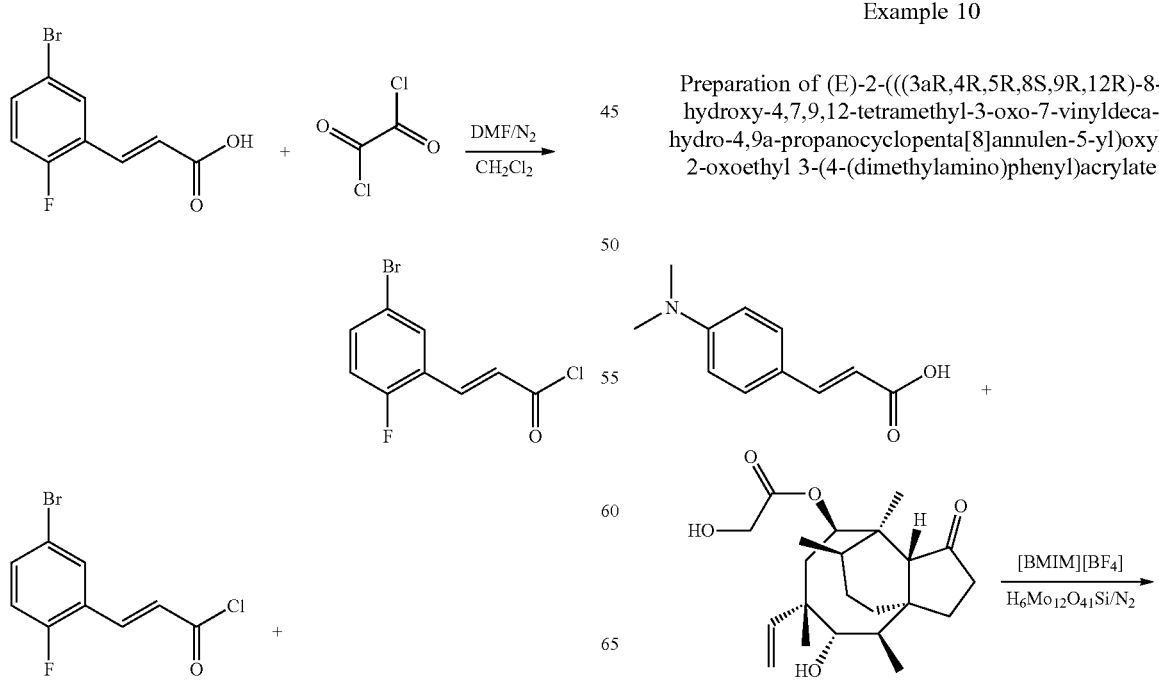

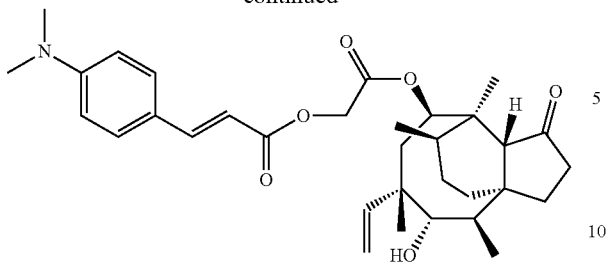
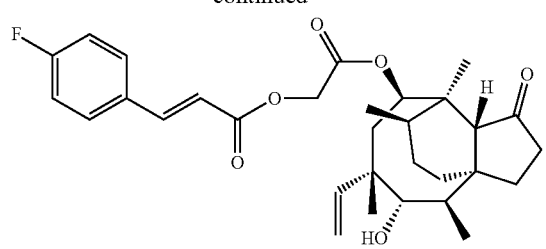

The target compound was prepared in a similar way as Example 3. The yield is 505.9 mg, 91.7%.

$^1$H NMR (400 MHz, CDCl$_3$) δ 7.73 (d, J=15.8 Hz, 1H), 7.46 (d, J=8.3 Hz, 2H), 6.73 (d, J=8.4 Hz, 2H), 6.53 (dd, J=17.5, 11.0 Hz, 1H), 6.32 (d, J=15.9 Hz, 1H), 5.84 (d, J=8.6 Hz, 1H), 5.39 (d, J=10.9 Hz, 1H), 5.25 (d, J=17.4 Hz, 1H), 4.66 (dd, J=16.0 Hz, 2H), 3.40 (s, 1H), 3.07 (s, 6H), 2.38 (t, J=7.2 Hz, 1H), 2.31-2.18 (m, 2H), 2.17-2.02 (m, 2H), 1.85-1.52 (m, 6H), 1.49 (s, 3H), 1.42 (d, J=15.7 Hz, 2H), 1.22 (s, 3H), 1.11 (d, J=18.5 Hz, 1H), 0.92 (d, J=7.0 Hz, 3H), 0.84 (d, J=6.9 Hz, 3H).

$^{13}$C NMR (101 MHz, CDCl$_3$) δ 217.04, 167.21, 166.83, 146.72, 138.83, 130.01, 117.39, 111.99, 111.00, 74.60, 69.48, 61.12, 58.13, 45.46, 44.57, 44.04, 41.89, 40.26, 36.75, 36.03, 34.48, 30.44, 26.84, 26.36, 24.84, 16.68, 14.82, 11.49.

The target compound was prepared in a similar way as Example 1. The yield is 498.4 mg, 91.5%.

$^1$H NMR (400 MHz, CDCl$_3$) δ 7.82 (d, J=16.0 Hz, 1H), 7.71-7.66 (m, 4H), 6.62 (d, J=15.9 Hz, 1H), 6.56-6.48 (m, 1H), 5.86 (t, J=8.4 Hz, 1H), 5.39 (d, J=11.1 Hz, 1H), 5.26 (d, J=17.4 Hz, 1H), 4.70 (dd, J=23.4, 2.7 Hz, 2H), 3.40 (s, 1H), 2.37 (t, J=7.2 Hz, 1H), 2.30-2.18 (m, 2H), 2.16-2.10 (m, 3H), 1.83-1.51 (m, 7H), 1.49 (s, 3H), 1.45-1.39 (m, 2H), 1.22 (s, 3H), 0.92 (d, J=7.4 Hz, 3H), 0.83 (d, J=7.0 Hz, 3H).

$^{13}$C NMR (101 MHz, CDCl$_3$) δ 216.91, 166.65, 165.46, 144.32, 138.78, 137.49, 128.35, 125.96, 125.92, 119.36, 117.40, 74.58, 69.83, 61.51, 58.10, 45.45, 44.62, 44.05, 41.89, 41.52, 36.69, 36.05, 34.45, 30.41, 26.83, 26.41, 24.83, 16.64, 14.79, 11.48.

Example 11

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(4-fluorophenyl)acrylate Example 12

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(2,3,4-trifluorophenyl)acrylate

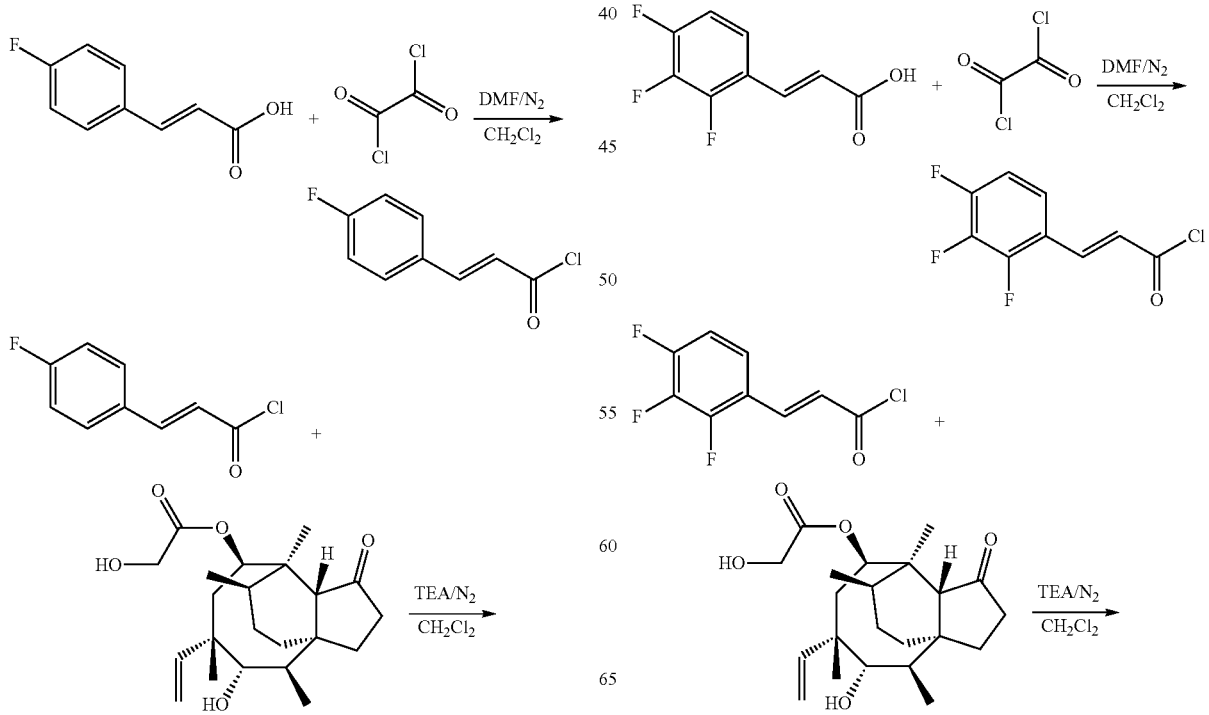

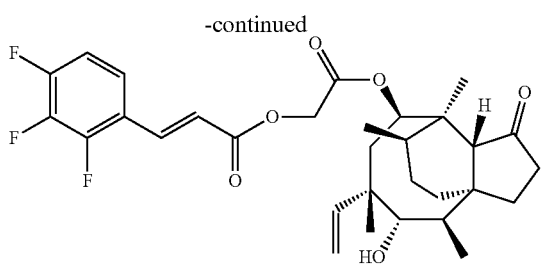

The target compound was prepared in a similar way as Example 1. The yield is 506.3 mg, 90.0%.

¹H NMR (400 MHz, CDCl3) δ 7.72 (d, J=16.0 Hz, 1H), 7.40 (t, J=9.3 Hz, 1H), 7.28-7.21 (m, 1H), 6.60-6.51 (m, 1H), 6.48 (d, J=16.6 Hz, 1H), 5.86 (d, J=8.5 Hz, 1H), 5.41 (d, J=11.0 Hz, 1H), 5.27 (d, J=17.4 Hz, 1H), 4.70 (dd, J=40.8, 16.0 Hz, 2H), 3.41 (d, J=6.5 Hz, 1H), 2.38 (t, J=6.8 Hz, 1H), 2.32-2.19 (m, 2H), 2.18-2.08 (m, 2H), 1.84-1.53 (m, 7H), 1.50 (s, 3H), 1.47-1.39 (m, 2H), 1.23 (s, 3H), 0.93 (d, J=6.9 Hz, 3H), 0.84 (d, J=6.9 Hz, 3H).

¹³C NMR (101 MHz, CDCl₃) δ 216.99, 166.72, 165.55, 143.86, 138.77, 131.37, 125.04, 118.04, 117.90, 117.45, 116.60, 116.42, 74.60, 69.79, 61.47, 58.11, 45.47, 44.61, 44.05, 41.89, 36.71, 36.05, 34.47, 30.43, 26.84, 26.39, 24.85, 16.67, 14.81, 11.50.

Example 13

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(3-(benzyloxy)phenyl)acrylate

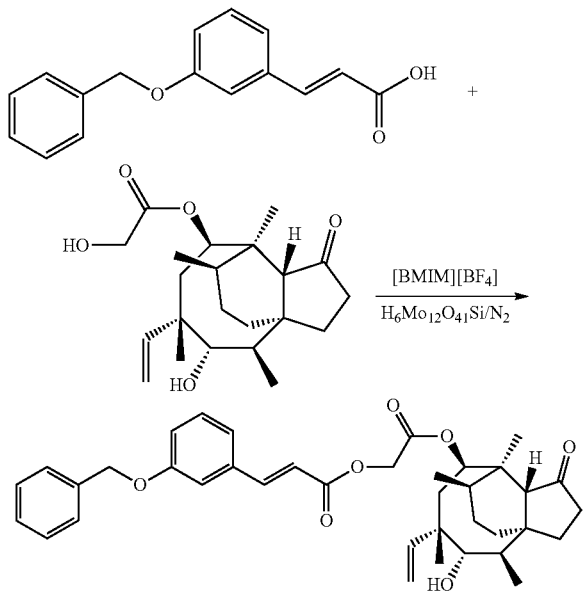

The target compound was prepared in a similar way as Example 3. The yield is 557.0 mg, 90.6%.

¹H NMR (400 MHz, CDCl₃) δ 7.76 (d, J=16.0 Hz, 1H), 7.56-7.32 (m, 5H), 7.30 (s, 1H), 7.17 (d, J=2.5 Hz, 2H), 7.06 (d, J=8.8 Hz, 1H), 6.55 (d, J=11.0 Hz, 1H), 6.51 (d, J=9.9 Hz, 1H), 5.86 (d, J=8.6 Hz, 1H), 5.40 (d, J=11.0 Hz, 1H), 5.26 (d, J=17.5 Hz, 1H), 5.13 (s, 2H), 4.69 (d, J=16.0 Hz, 2H), 3.41 (d, J=6.4 Hz, 1H), 2.38 (t, J=6.9 Hz, 1H), 2.30-2.17 (m, 2H), 2.17-2.07 (m, 2H), 1.87-1.51 (m, 6H), 1.49 (s, 3H), 1.46-1.37 (m, 2H), 1.23 (s, 3H), 1.16 (dd, J=14.2, 4.5 Hz, 1H), 0.93 (d, J=7.0 Hz, 3H), 0.84 (d, J=6.9 Hz, 3H).

¹³C NMR (101 MHz, CDCl₃) δ 216.73, 166.81, 166.02, 159.17, 146.12, 138.82, 136.65, 135.61, 129.99, 128.67, 128.12, 127.47, 121.20, 117.40, 117.13, 114.21, 74.62, 70.65, 70.17, 61.39, 58.13, 45.45, 44.79, 44.03, 41.96, 41.50, 36.70, 36.06, 34.43, 30.42, 26.85, 26.39, 24.85, 16.73, 14.80, 11.46.

Example 14

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-([1,1'-biphenyl]-3-yl)acrylate

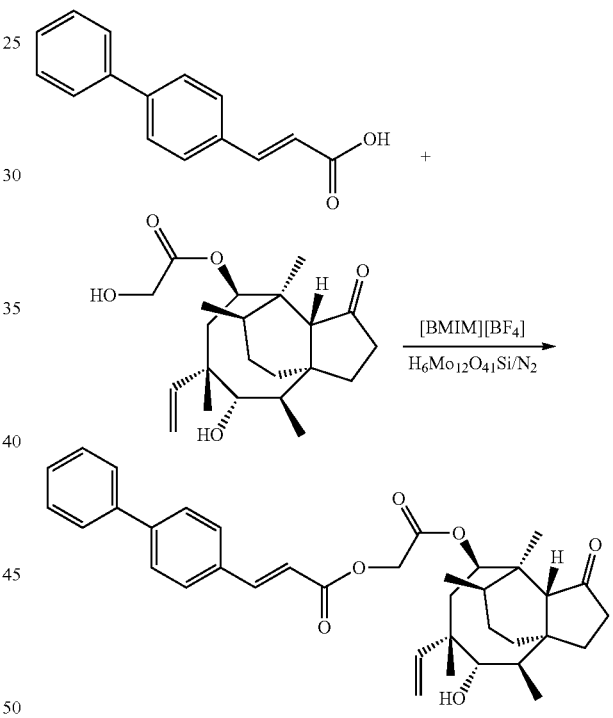

The target compound was prepared in a similar way as Example 3. The yield is 533.3 mg, 91.2%.

¹H NMR (400 MHz, CDCl₃) δ 7.86 (d, J=15.9 Hz, 1H), 7.70-7.63 (m, 6H), 7.51 (t, J=7.5 Hz, 2H), 7.42 (t, J=7.4 Hz, 1H), 6.64-6.49 (m, 2H), 5.87 (d, J=8.4 Hz, 1H), 5.41 (d, J=11.0 Hz, 1H), 5.27 (d, J=17.6 Hz, 1H), 4.71 (d, J=9.0 Hz, 2H), 3.41 (d, J=6.4 Hz, 1H), 2.38 (t, J=7.0 Hz, 1H), 2.26 (p, J=10.2, 9.6 Hz, 2H), 2.13 (d, J=18.6 Hz, 2H), 1.87-1.53 (m, 7H), 1.51 (s, 3H), 1.49-1.39 (m, 2H), 1.23 (s, 3H), 0.93 (d, J=6.8 Hz, 3H), 0.86 (d, J=6.9 Hz, 3H).

¹³C NMR (101 MHz, CDCl₃) δ 216.96, 166.88, 166.06, 145.80, 143.40, 140.10, 138.82, 133.13, 128.93, 128.76, 127.93, 127.61, 127.08, 117.41, 116.57, 74.60, 70.85, 61.39, 57.75, 45.89, 44.63, 44.06, 41.91, 37.31, 36.05, 34.47, 30.05, 26.86, 26.40, 24.85, 16.68, 14.82, 11.48.

Example 15

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(4-(trifluoromethyl)phenyl)acrylate

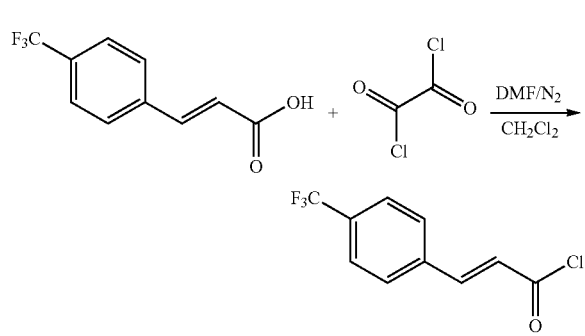

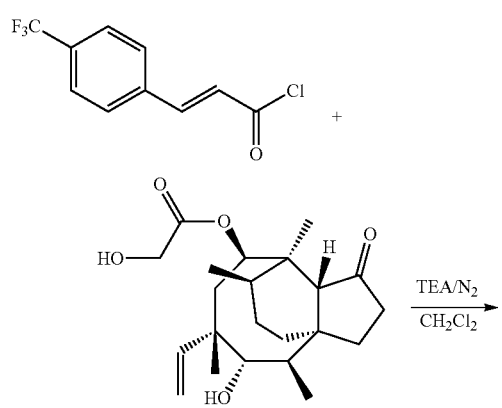

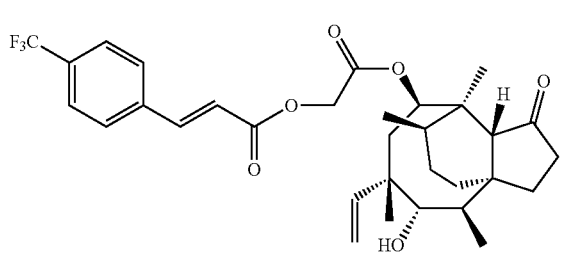

The target compound was prepared in a similar way as Example 1. The yield is 528.3 mg, 91.6%.

$^1$H NMR (400 MHz, CDCl$_3$) δ 7.82 (d, J=16.0 Hz, 1H), 7.68 (d, J=3.2 Hz, 4H), 6.62 (d, J=15.9 Hz, 1H), 6.57-6.48 (m, 1H), 5.86 (d, J=8.4 Hz, 1H), 5.39 (d, J=11.1 Hz, 1H), 5.26 (d, J=17.4 Hz, 1H), 4.70 (dd, J=23.4, 2.7 Hz, 2H), 3.40 (s, 1H), 2.42-2.33 (m, 1H), 2.30-2.18 (m, 2H), 2.13 (q, J=8.5, 7.0 Hz, 2H), 1.86-1.51 (m, 7H), 1.49 (s, 3H), 1.46-1.34 (m, 2H), 1.22 (s, 3H), 0.92 (d, J=7.4 Hz, 3H), 0.83 (d, J=7.0 Hz, 3H).

$^{13}$C NMR (101 MHz, CDCl$_3$) δ 216.91, 166.65, 165.46, 144.32, 138.78, 137.49, 128.35, 125.96, 125.92, 119.36, 117.40, 74.58, 69.83, 61.51, 58.10, 45.45, 44.62, 44.05, 41.89, 41.52, 36.69, 36.05, 34.45, 30.41, 26.83, 26.41, 24.83, 16.64, 14.79, 11.48.

Example 16

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(3-(trifluoromethyl)phenyl)acrylate

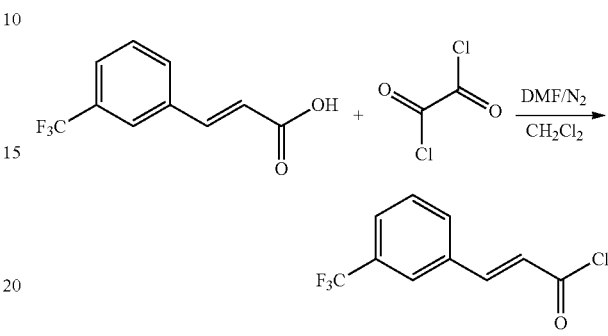

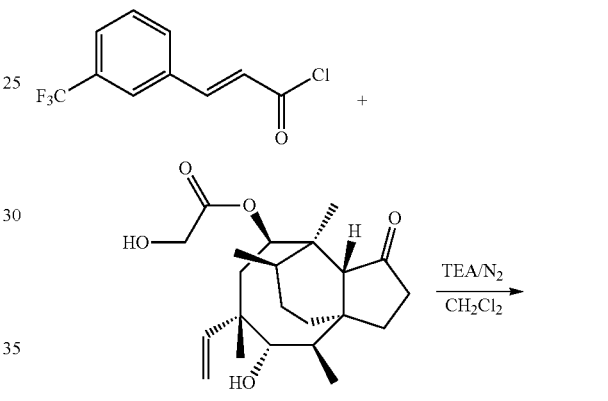

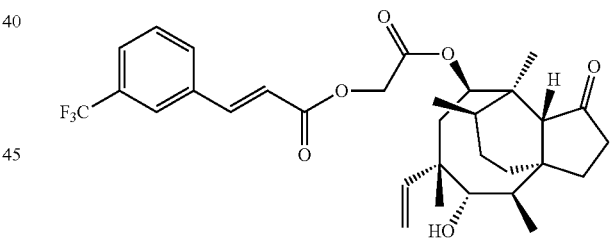

The target compound was prepared in a similar way as Example 1. The yield is 532.3 mg, 92.3%.

$^1$H NMR (400 MHz, CDCl$_3$) δ 7.82 (d, J=13.5 Hz, 2H), 7.74 (d, J=7.8 Hz, 1H), 7.69 (d, J=7.9 Hz, 1H), 7.57 (t, J=7.9 Hz, 1H), 6.61 (d, J=15.7 Hz, 1H), 6.52 (dd, J=17.6, 11.2 Hz, 1H), 5.86 (d, J=8.3 Hz, 1H), 5.39 (d, J=10.8 Hz, 1H), 5.26 (d, J=17.6 Hz, 1H), 4.77-4.64 (m, 2H), 3.40 (d, J=6.4 Hz, 1H), 2.37 (t, J=7.2 Hz, 1H), 2.31-2.19 (m, J=9.5 Hz, 2H), 2.17-2.08 (m, 2H), 1.87-1.51 (m, 6H), 1.49 (s, 3H), 1.47-1.37 (m, 2H), 1.22 (s, 3H), 1.20-1.12 (m, 1H), 0.92 (d, J=6.8 Hz, 3H), 0.83 (d, J=6.9 Hz, 3H).

$^{13}$C-NMR (101 MHz, CDCl$_3$) δ (ppm): 216.80, 166.62, 165.43, 144.29, 138.82, 137.53, 128.33, 125.95, 125.91, 119.41, 117.36, 74.61, 69.86, 61.52, 60.36, 58.11, 45.46, 44.67, 44.07, 41.91, 36.70, 36.07, 34.43, 30.43, 26.85, 26.43, 24.84, 21.00, 16.62, 14.79, 14.18, 11.42.

Example 17

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(4-(1H-imidazol-1-yl)phenyl)acrylate

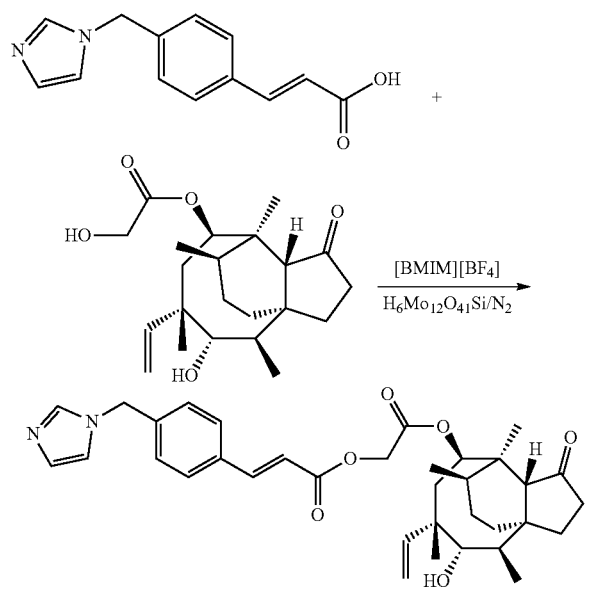

The target compound was prepared in a similar way as Example 3. The yield is 527.6 mg, 89.6%.

$^1$H NMR (400 MHz, CDCl$_3$) δ 7.78 (d, J=16.0 Hz, 1H), 7.66 (s, 1H), 7.56 (d, J=7.8 Hz, 2H), 7.22 (d, J=7.7 Hz, 2H), 7.16 (s, 1H), 6.96 (s, 1H), 6.53 (t, J=14.9 Hz, 2H), 5.85 (d, J=8.6 Hz, 1H), 5.39 (d, J=10.9 Hz, 1H), 5.26 (d, J=17.4 Hz, 1H), 5.20 (s, 2H), 4.69 (d, J=16.0 Hz, 2H), 3.41 (d, J=6.3 Hz, 1H), 2.37 (t, J=7.5 Hz, 1H), 2.32-2.17 (m, 2H), 2.19-2.06 (m, 2H), 1.88-1.50 (m, 6H), 1.48 (s, 3H), 1.46-1.34 (m, 2H), 1.22 (s, 3H), 1.20-1.12 (m, 1H), 0.92 (d, J=6.9 Hz, 3H), 0.83 (d, J=7.0 Hz, 3H).

$^{13}$C NMR (101 MHz, CDCl$_3$) δ 217.02, 166.77, 165.81, 145.17, 138.81, 138.54, 137.44, 134.25, 129.75, 128.80, 127.75, 119.33, 117.50, 117.37, 74.55, 69.76, 61.40, 58.10, 50.48, 45.45, 44.59, 44.04, 41.88, 36.69, 36.04, 34.46, 30.41, 26.83, 26.43, 24.82, 16.65, 14.79, 11.48.

Example 18

Preparation of (E)-2-(((3aR,4R,5R,7S,8S,9R,9aS,12R)-8-hydroxy-4,7,9,12-tetramethyl-3-oxo-7-vinyl-decahydro-4,9a-propanocyclopenta[8]annulen-5-yl)oxy)-2-oxoethyl 3-(naphthalen-2-yl)acrylate

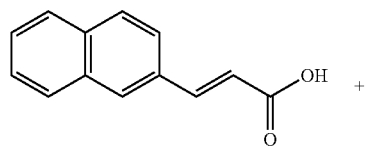

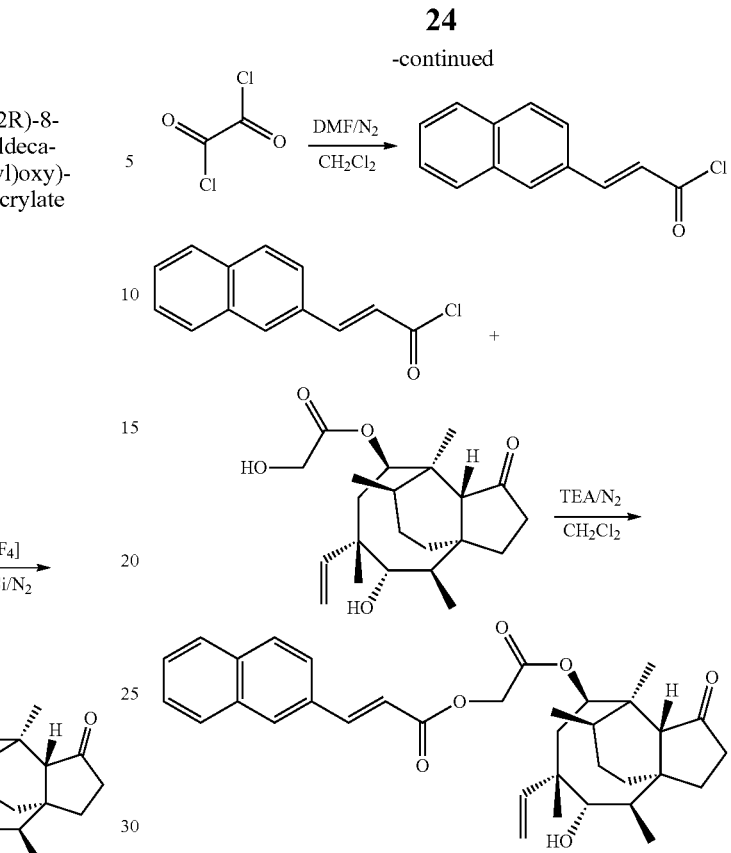

The target compound was prepared in a similar way as Example 1. The yield is 515.7 mg, 92.3%.

$^1$H NMR (400 MHz, CDCl$_3$) δ 8.65 (d, J=15.7 Hz, 1H), 8.22 (d, J=8.3 Hz, 1H), 7.93 (dd, J=12.7, 8.3 Hz, 2H), 7.81 (d, J=7.2 Hz, 1H), 7.64-7.51 (m, 3H), 6.64 (d, J=15.8 Hz, 1H), 6.55 (dd, J=17.5, 11.1 Hz, 1H), 5.87 (d, J=8.5 Hz, 1H), 5.41 (d, J=10.9 Hz, 1H), 5.27 (d, J=17.4 Hz, 1H), 4.82-4.66 (m, 2H), 3.40 (d, J=6.3 Hz, 1H), 2.38 (t, J=7.1 Hz, 1H), 2.29-2.20 (m, 2H), 2.17-2.11 (m, 2H), 1.83-1.55 (m, 6H), 1.51-1.41 (m, 6H), 1.23 (s, 3H), 0.91 (d, J=6.8 Hz, 4H), 0.86 (d, J=7.0 Hz, 3H).

$^{13}$C NMR (101 MHz, CDCl$_3$) δ 217.00, 166.87, 165.92, 143.28, 138.81, 133.68, 131.47, 131.41, 130.89, 128.79, 127.00, 126.31, 125.49, 125.26, 123.32, 119.31, 117.45, 74.60, 69.73, 61.45, 58.12, 45.47, 44.62, 44.07, 41.92, 36.73, 36.05, 34.47, 30.43, 26.86, 26.40, 24.84, 16.71, 14.84, 11.50.

Example 19

Preparation of (E)-2-(((3aR,4R,5R,8S,9R,12R)-8-hydroxy-4,7,9,12-tetramethyl-3-oxo-7-vinyldecahydro-4,9a-propanocyclopenta[8]annulen-5-yl)oxy)-2-oxoethyl 3-(2-fluoro-4-(trifluoromethyl)phenyl)acrylate

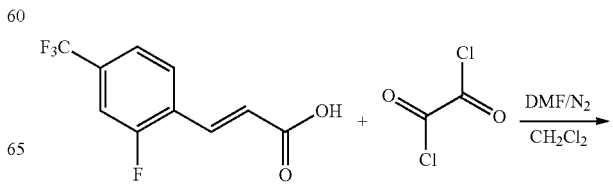

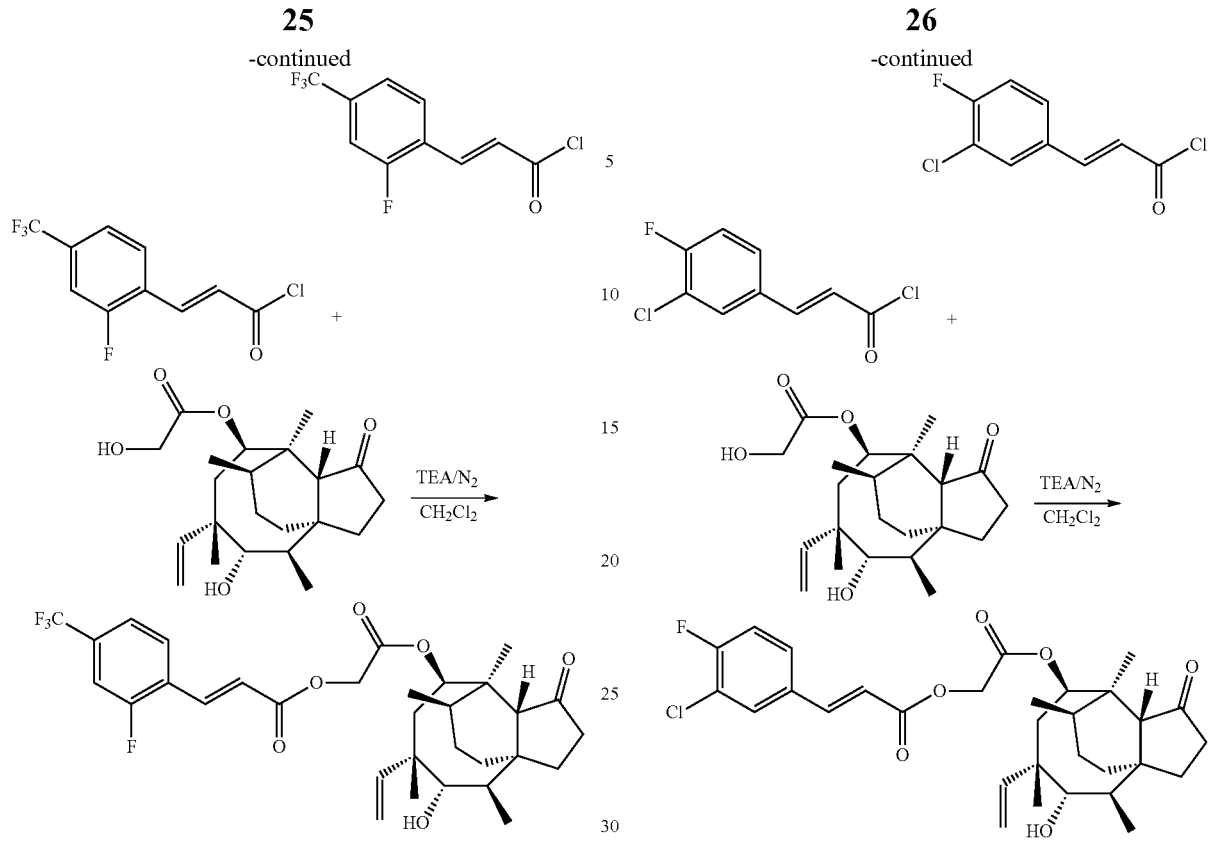

The target compound was prepared in a similar way as Example 1. The yield is 542.3 mg, 91.2%.

$^1$H NMR (400 MHz, CDCl$_3$) δ 7.91 (d, J=16.2 Hz, 1H), 7.70 (t, J=7.6 Hz, 1H), 7.49 (d, J=8.2 Hz, 1H), 7.42 (d, J=10.4 Hz, 1H), 6.72 (d, J=16.2 Hz, 1H), 6.51 (dd, J=17.5, 11.0 Hz, 1H), 5.85 (d, J=8.4 Hz, 1H), 5.39 (d, J=10.9 Hz, 1H), 5.26 (d, J=17.4 Hz, 1H), 4.70 (dd, J=16.0 Hz, 2H), 3.41 (d, J=6.4 Hz, 1H), 2.37 (t, J=7.0 Hz, 1H), 2.26 (q, J=9.8, 9.4 Hz, 2H), 2.21-2.05 (m, 2H), 1.88-1.51 (m, 6H), 1.49 (s, 3H), 1.41 (d, J=16.2 Hz, 2H), 1.22 (s, 3H), 1.16 (d, J=16.4 Hz, 1H), 0.92 (d, J=6.9 Hz, 3H), 0.83 (d, J=6.9 Hz, 3H).

$^{13}$C NMR (101 MHz, CDCl$_3$) δ 216.93, 166.57, 165.30, 162.09, 159.55, 138.76, 137.08, 129.79, 125.76, 121.87, 121.80, 121.41, 117.41, 113.99, 74.57, 69.85, 61.57, 58.08, 45.45, 44.60, 44.04, 41.88, 36.68, 36.04, 34.45, 30.40, 26.83, 26.39, 24.83, 16.64, 14.78, 11.47.

The target compound was prepared in a similar way as Example 1. The yield is 517.9 mg, 92.3%.

$^1$H NMR (400 MHz, CDCl$_3$) δ 7.70 (d, J=16.0 Hz, 1H), 7.62 (d, J=6.9 Hz, 1H), 7.45 (t, J=6.9 Hz, 1H), 7.22 (t, J=8.6 Hz, 1H), 6.58-6.44 (m, 2H), 5.85 (d, J=8.4 Hz, 1H), 5.40 (d, J=11.0 Hz, 1H), 5.26 (d, J=17.4 Hz, 1H), 4.69 (d, J=16.0 Hz, 2H), 3.41 (d, J=6.4 Hz, 1H), 2.41-2.33 (m, 1H), 2.32-2.17 (m, 2H), 2.12 (d, J=18.9 Hz, 2H), 1.86-1.50 (m, 6H), 1.49 (s, 3H), 1.41 (d, J=15.8 Hz, 2H), 1.22 (s, 3H), 1.16 (dd, J=14.1, 4.1 Hz, 1H), 0.92 (d, J=6.8 Hz, 3H), 0.83 (d, J=6.9 Hz, 3H).

$^{13}$C NMR (101 MHz, CDCl$_3$) δ 216.98, 166.69, 165.52, 143.57, 138.77, 131.53, 130.24, 128.18, 128.11, 117.90, 117.43, 117.35, 117.13, 74.58, 69.77, 61.46, 58.09, 45.45, 44.60, 44.04, 41.88, 36.69, 36.03, 34.46, 30.41, 26.83, 26.39, 24.83, 16.65, 14.80, 11.48.

Example 20

Preparation of (E)-2-(((3aR,4R,5R,8S,9R,12R)-8-hydroxy-4,7,9,12-tetramethyl-3-oxo-7-vinyldeca-hydro-4,9a-propanocyclopenta[8]annulen-5-yl)oxy)-2-oxoethyl 3-(3-chloro-4-fluorophenyl)acrylate Example 21

Preparation of (E)-2-(((3aR,4R,5R,8S,9R,12R)-8-hydroxy-4,7,9,12-tetramethyl-3-oxo-7-vinyldeca-hydro-4,9a-propanocyclopenta[8]annulen-5-yl)oxy)-2-oxoethyl 3-(2-fluorophenyl)acrylate

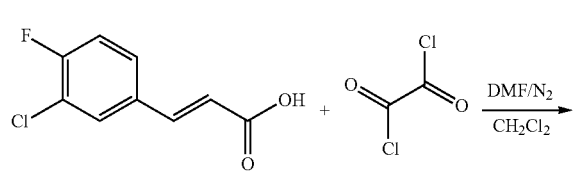

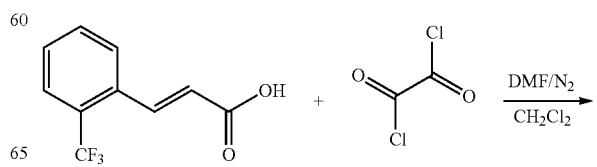

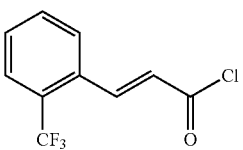

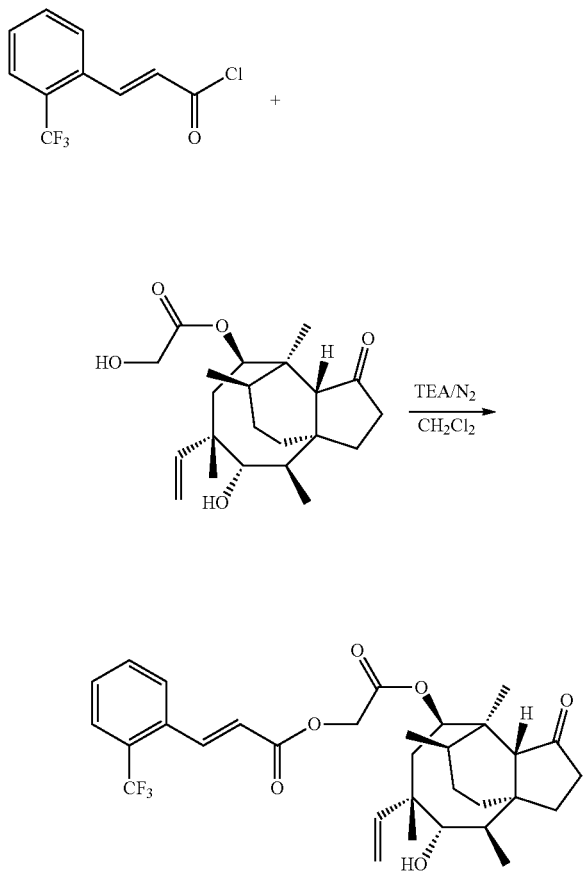

The target compound was prepared in a similar way as Example 1. The yield is 474.6 mg, 82.3%.

$^1$H NMR (400 MHz, CDCl$_3$) δ 8.17 (d, J=15.8 Hz, 1H), 7.75 (d, J=7.7 Hz, 2H), 7.62 (t, J=7.8 Hz, 1H), 7.54 (t, J=7.9 Hz, 1H), 6.56-6.49 (m, 2H), 5.85 (d, J=8.5 Hz, 1H), 5.40 (d, J=11.0 Hz, 1H), 5.26 (d, J=17.4 Hz, 1H), 4.79-4.62 (m, 2H), 3.40 (s, 1H), 2.37 (t, J=7.2 Hz, 1H), 2.29-2.20 (m, 2H), 2.14-2.09 (m, 2H), 1.83-1.52 (m, 7H), 1.48 (s, 3H), 1.41 (d, J=16.1 Hz, 2H), 1.22 (s, 3H), 0.91 (d, J=6.8 Hz, 3H), 0.83 (d, J=6.8 Hz, 3H).

$^{13}$C NMR (101 MHz, CDCl$_3$) δ 216.99, 166.65, 165.14, 141.66, 138.76, 133.08, 132.18, 129.89, 127.99, 126.26, 126.20, 125.22, 121.12, 117.43, 74.59, 69.78, 61.54, 58.10, 45.45, 44.56, 44.04, 41.88, 36.70, 36.03, 34.46, 30.42, 26.84, 26.36, 24.83, 16.64, 14.75, 11.48.

2. Measuring In Vitro Activities Against Antibiotic-Resistant Infections

The minimum inhibitory concentration (MIC) of pleuromutilin cinnamate easters and their starting materials was tested by a micro-broth dilution method, with retamoline, vornimulin and tiamulin as positive controls.

The experimental strains included Gram-positive bacteria: Methicillin-sensitive *Staphylococcus epidermidis* ATCC12228, *Staphylococcus aureus* ATCC29213 and ATCC25923, and Methicillin-resistant *Staphylococcus aureus* ATCC33591; Gram-negative bacteria: *Acinetobacter baumannii* ATCC19606 and *E. coli Bacillus* ATCC25922 (the strains used were from the American type culture collection (ATCC)).

The specific experimental steps are as follows:

(1) Preparation of MHB medium: Weighing 20.0 g of MHB medium (purchased from Shanghai Jizhi Biochemical Technology Co., Ltd.), adding it to 1 L of distilled water, heating and boiling until it was completely dissolved, and then storing it into a conical flask, under high pressure at 121° C., sterilizing for 15 min;

(2) The experimental strain was cultivated to a logarithmic growth phase: under sterile conditions, the experimental strain was inoculated into 100 mL of MHB medium, and placed in a constant temperature and humidity incubator at 37° C. for 20-22 h;

(3) Preparation of stock (test and control) solutions: Weighing a sample to be tested, dissolving it with 1% DMSO solution, and preparing a test solution with a concentration of 5120 g/mL; weighing a positive reference substance, dissolve it in sterile distilled water, and preparing a control solution with a concentration of 5120 μg/mL;

(4) Bacterial suspension preparation: Under sterile conditions, the experimental strains cultivated to the logarithmic growth phase were adjusted to a turbidity standard of 0.5 McFarland units with the MHB medium, and then diluted at a ratio of 1:200 for use;

(5) Dilution of stock solution and inoculation of experimental strains: taking a sterile 96-well plate, adding 10 μL MHB medium to wells 4-11 under sterile conditions; adding 10 μL positive control solution to well 2, and adding 10 μL positive control solution to well 3, adding L of test solution to well 4, mixing the test solution in well 4 with culture medium, then pipetting 10 μL to well 5, mixing well and pipetting 10 μL to well 6, and so serially dilute to the 10th well, and discarding 10 μL from the 10th well, and the 11th well was the solvent control; then, adding 190 μL of the above-prepared bacterial suspension to each well, so that the final bacterial concentration of each well was 5×10$^5$ CFU/mL; the concentration of the positive control was 256 μg/mL, and the concentration of the test solution is 256, 128, 64, 32, 16, 8, 4, and 2 μg/mL.

(6) Incubation: covering the 96-well plate inoculated with the experimental strain, and place it in a constant temperature and humidity box at 37° C. for 20-22 h;

(7) Interpretation of the MIC endpoint: the concentration that can completely inhibit the growth of bacteria observed in the 96-well plate under a black background is the minimum inhibitory concentration of the sample against this type of bacteria. The recorded results are shown in Table 1.

TABLE 1

Minimum inhibitory concentrations of tested compounds and controls (μg · mL$^{-1}$)

| | Bacteria | | | | | |
|---|---|---|---|---|---|---|
| | Methicillin-sensitive *Staphylococcus epidermidis* | *Staphylococcus aureus* | | Methicillin-resistant *Staphylococcus aureus* | *Escherichia coli* | *Acinetobacter baumannii* |
| Comp. | ATCC12228 | ATCC25923 | ATCC29213 | ATCC33591 | ATCC25922 | ATCC19606 |
| Retapamulin | 32 | 4 | 4 | 32 | 32 | 16 |
| Tiamulin | 16 | 64 | 256 | 128 | 128 | 64 |
| Valnemulin | 64 | 4 | 2 | >256 | 16 | 2 |
| 1 | 2 | 8 | 2 | 4 | 32 | 64 |
| 2 | 8 | 16 | 32 | 32 | 64 | 128 |
| 3 | 16 | 4 | 16 | 32 | 128 | >256 |
| 4 | 2 | 4 | 8 | 16 | 32 | >256 |
| 5 | 2 | 2 | 8 | 16 | 64 | 128 |
| 6 | 64 | 32 | 64 | 64 | >256 | >256 |
| 7 | 16 | 4 | 8 | 32 | 64 | >256 |
| 8 | 32 | 16 | 32 | 64 | >256 | >256 |
| 9 | 64 | 16 | 32 | 64 | 64 | 128 |
| 10 | 1 | 1 | 2 | 2 | 16 | 32 |
| 11 | 32 | 16 | 32 | 32 | 128 | 128 |
| 12 | 16 | 32 | 64 | 128 | 64 | 128 |
| 13 | 32 | 16 | 32 | 128 | >256 | 64 |
| 14 | 32 | 64 | 32 | 64 | >256 | >256 |
| 15 | 8 | 16 | 16 | 128 | 64 | >256 |
| 16 | 64 | 32 | 64 | 256 | 64 | 128 |
| 17 | 16 | 8 | 16 | 32 | 64 | 128 |
| 18 | 32 | 16 | 32 | 128 | 256 | 256 |
| 19 | 16 | 8 | 16 | 64 | 128 | >256 |
| 20 | 32 | 16 | 32 | 64 | 64 | >256 |
| 21 | 64 | 32 | 64 | 128 | >256 | >256 |

It can be seen from Table 1 that the compounds 1 to 21 can inhibit the methicillin-sensitive *Staphylococcus epidermidis* ATCC25923. Compared with the three tested positive controls, compounds 1, 2, 4, 5, 10, and 15 have inhibitory effects. The bacterial effect was better than that of the positive controls. Compounds 1 to 21 all had inhibitory effects on *Staphylococcus aureus* ATCC25293, *Staphylococcus aureus* ATCC29213 and methicillin-resistant *Staphylococcus aureus* ATCC33591, especially compound 10. Most of the compounds 1 to 21 can inhibit *E. coli Bacillus* and: *Acinetobacter baumannii*. The degree of inhibition was comparable to that of vornimulin. Although the inhibitory degree of the compounds against *Acinetobacter baumannii* was not as good as that of vornimulin, which had the best effect among the three positive controls, compounds 1, 10, and 13 can inhibit *Acinetobacter baumannii* as much as tiamulin. It can be seen that the inhibitory activity of compound 10 on the different bacteria tested is better or equal to that of the three tested positive controls, and further clinical research can be done.

3. Determination of Cytotoxicity of Compounds

The in vitro cytotoxicity of pleuromutilin easters was determined by a CCK-8 method (the kit used was purchased from Shanghai Xige Biotechnology Co., Ltd.). Take healthy HepG2, HEK293 and A549 cell culture fluids (the cells used were from the American type culture collection (ATCC), and the used cell culture fluids were purchased from Thermo Fisher Scientific (China) Co., Ltd.), inoculate in a sterile 96-well cell culture plate, 180 μL/well, ensure that the number of cells is $1*10^4$/well, place in a 37° C. $CO_2$ incubator with a volume fraction of 5%, and culture for 24 h until the cells completely adhered. Add the test and control solutions, 20 L per well, set 6 duplicate wells in parallel, and incubate at 37° C. in a $CO_2$ incubator with a volume fraction of 5% at 37° C. for 24 h, and observe the cells under a microscope. Add 20 μL of 5 g/L CCK-8 solution to each well, and continue to culture for 4 h. The culture was terminated, the culture medium in the wells was gently aspirated, 100 μL of dimethyl sulfoxide was added to each well, and the wells were shaken at low speed for 10 min on a shaker to fully dissolve the crystals. The absorbance value was measured, and the half inhibitory concentration ($IC_{50}$) was then calculated. The cytotoxicity to HepG2, HEK293 and A549 cells was evaluated according to the half inhibitory concentration ($IC_{50}$). Results are shown in Table 2.

TABLE 2

The median inhibitory concentration ($IC_{50}$) of the tested drugs and positive drugs (μM)

| | $IC_{50}$ Value | | |
|---|---|---|---|
| Tested Compounds | HepG2 | HEK293 | A549 |
| Retapamulin | 36.48 | 62.89 | 74.17 |
| Valnemulin | 37.26 | 31.1 | 46.21 |
| Tiamulin | 27.12 | 84.94 | >200 |
| Compound 1 | >200 | >200 | >200 |
| Compound 4 | 83.7 | 90.24 | 50.78 |
| Compound 5 | 78.5 | 29.18 | >200 |
| Compound 10 | >200 | 34.55 | >200 |

Table 2 shows the median inhibitory concentration ($IC_{50}$) of different test drugs, among which compound 1 has the least toxicity, and the $IC_{50}$ value for all three cells is greater than 200 μM, which is significantly higher than those of ritamulin, vornimulin and tiamulin. In addition, the cytotoxicity of compound 4 to HepG2 cells is 83.7 μM, which was 3.1 times higher that of tiamulin (IC$_{50}$=27.12 μM); the cytotoxicity of compound 4 to HEK293 cells is 90.24 μM, which is 2.9 times higher than that of vonimulin (IC$_{50}$=31.1 μM).

The above content is only to illustrate the technical idea of the present invention, and cannot limit the protection scope of the present invention. Any modification made on the basis of the technical solution proposed in accordance with the technical idea of the present invention falls within the scope of the claims of the present invention. within the scope of protection.

The invention claimed is:

1. A pleuromutilin cinnamic acid ester compound with activities against antibiotic-resistant infections having the following formula (I):

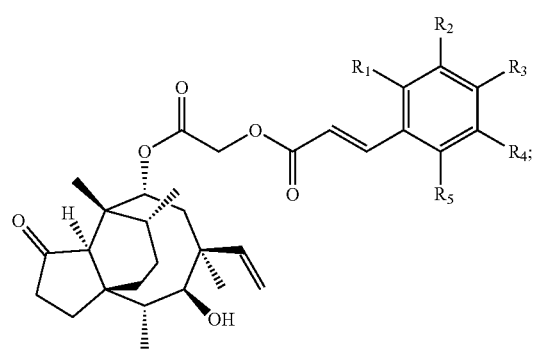

wherein $R_1$, $R_2$, $R_3$, $R_4$ and $R_5$ are independently selected from the group consisting of hydrogen, halogen, nitro, cyano, methoxy, trifluoromethyl, benzyloxy, aryl, imidazolidine, and dimethylamino.

2. The pleuromutilin cinnamic acid ester compound with activities against antibiotic-resistant infections according to claim 1, wherein the compound is selected from the group consisting of:

1

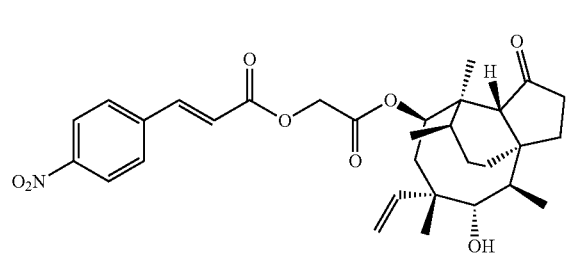

2

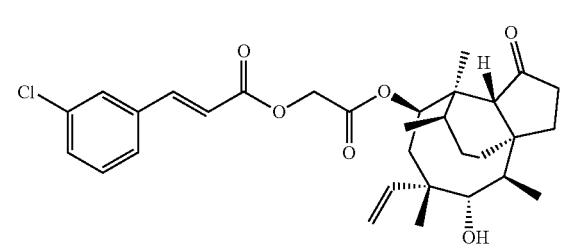

3

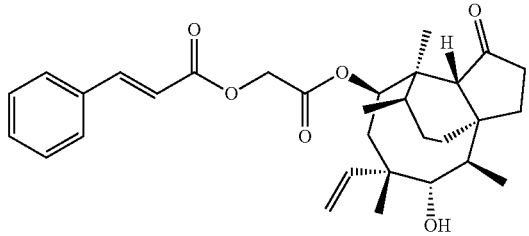

4

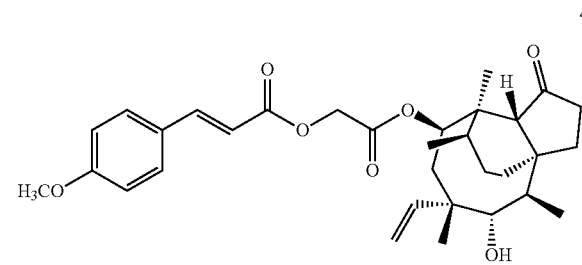

5

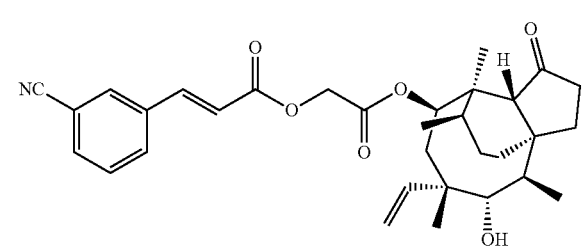

6

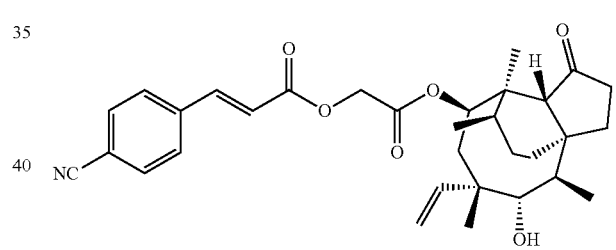

7

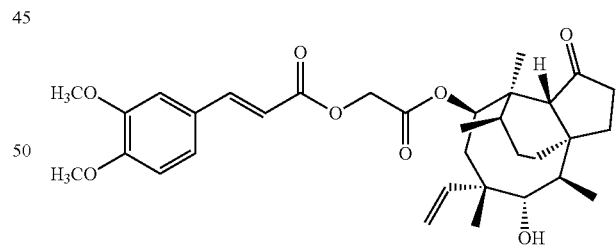

8

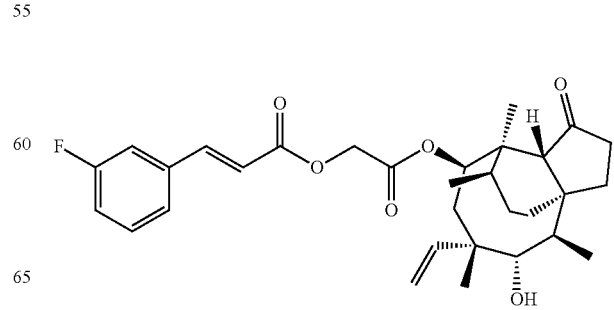

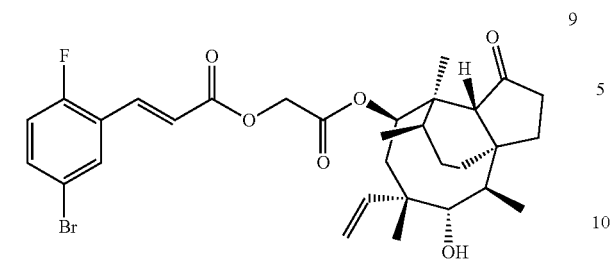
9
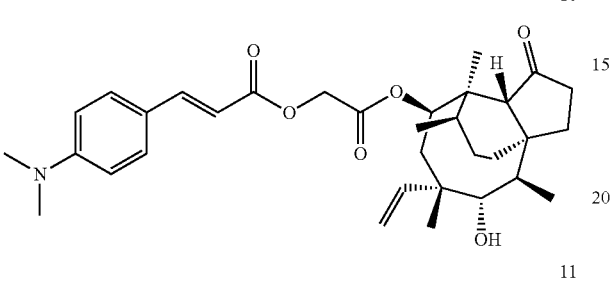
10
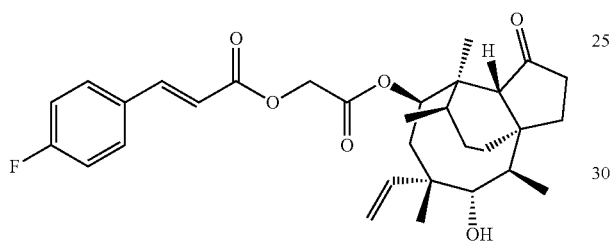
11
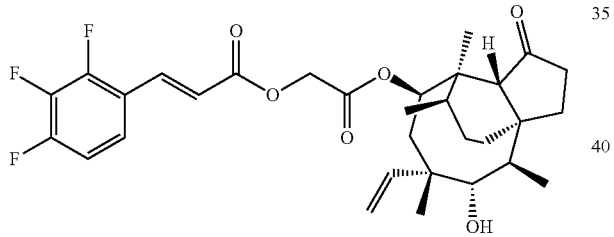
12
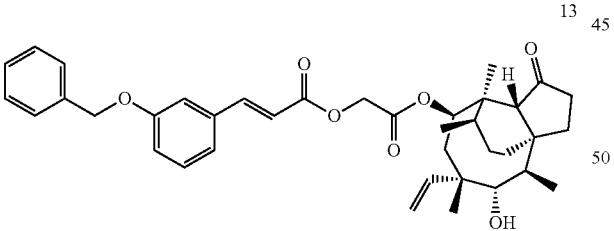
13
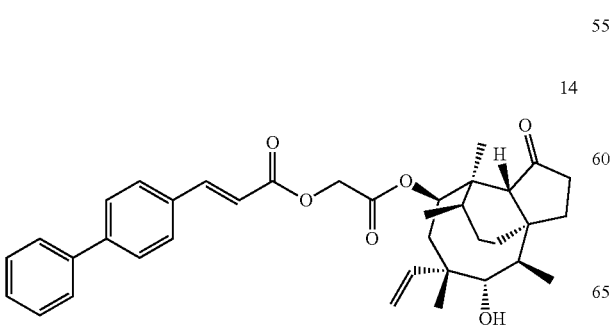
14
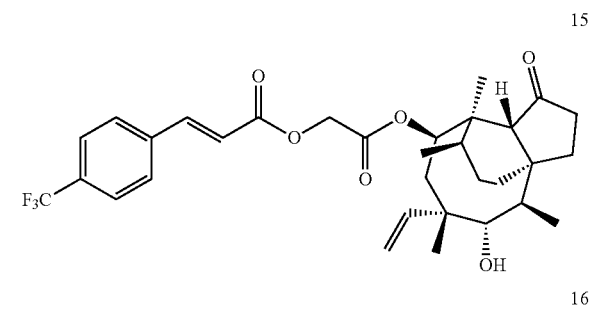
15
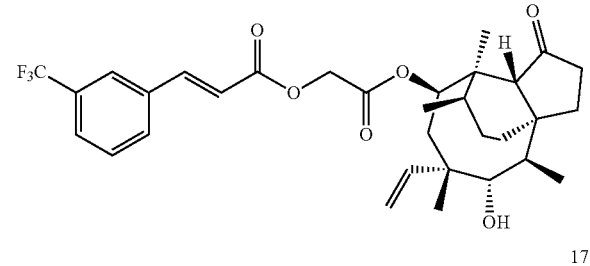
16
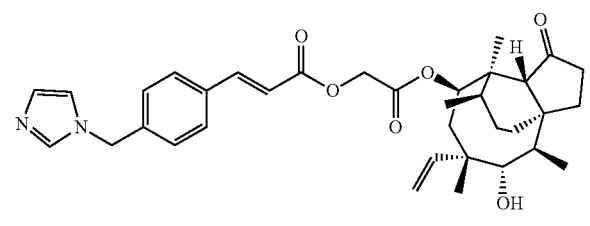
17
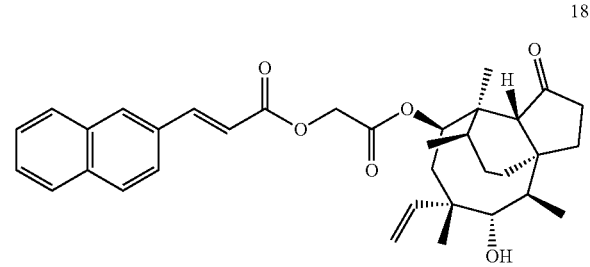
18
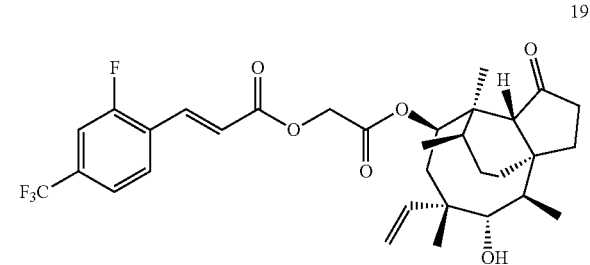
19
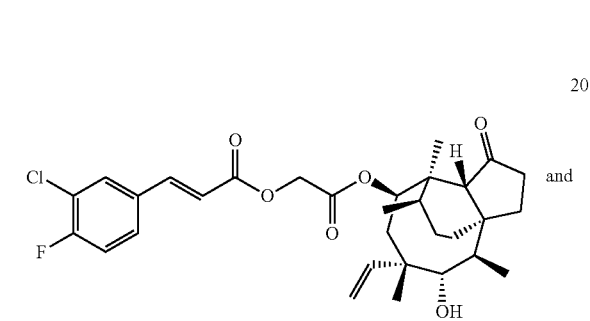
20

-continued
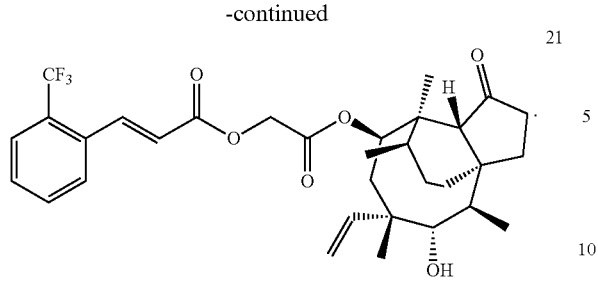
* * * * *